US012766021B2

(12) United States Patent
Bejarano et al.

(10) Patent No.: US 12,766,021 B2
(45) Date of Patent: Oct. 20, 2026

(54) ROTATING PLATFORM RIGID SHOULDER ORTHOSIS AND RELATED METHODS

(71) Applicant: DJO, LLC, Carlsbad, CA (US)

(72) Inventors: Robert Bejarano, Carlsbad, CA (US); Eileen Zirpolo-Kisco, Carlsbad, CA (US); Kyle Frank, Carlsbad, CA (US); Trevor Martin, Carlsbad, CA (US)

(73) Assignee: DJO, LLC, Carlsbad, CA (US)

( * ) Notice: Subject to any disclaimer, the term of this patent is extended or adjusted under 35 U.S.C. 154(b) by 0 days.

(21) Appl. No.: 18/791,025

(22) Filed: Jul. 31, 2024

(65) Prior Publication Data

US 2025/0041092 A1 Feb. 6, 2025

Related U.S. Application Data

(60) Provisional application No. 63/530,218, filed on Aug. 1, 2023.

(51) Int. Cl.
*A61F 5/01* (2006.01)
*A61F 5/37* (2006.01)

(52) U.S. Cl.
CPC .......... *A61F 5/0118* (2013.01); *A61F 5/3753* (2013.01); *A61F 2005/0158* (2013.01); *A61F 2005/0167* (2013.01)

(58) Field of Classification Search
CPC ........ A61F 5/0118; A61F 5/3753; A61F 5/01; A61F 5/37; A61F 5/013; A61F 5/3738;
(Continued)

(56) References Cited

U.S. PATENT DOCUMENTS 3,952,733 A * 4/1976 Williams .............. A61F 5/3753 602/4
4,836,195 A * 6/1989 Berrehail .............. A61F 5/3753 D24/190
(Continued)

FOREIGN PATENT DOCUMENTS

CA 2491509 C 7/2006
CN 101692988 B 4/2010
(Continued)

OTHER PUBLICATIONS

He et al., Translation of CN-211356128-U, retrieved from Espacenet.com (Year: 2020).*
(Continued)

*Primary Examiner* — Daniel A Miller
(74) *Attorney, Agent, or Firm* — Veros Legal Solutions, LLP

(57) ABSTRACT

An orthosis is provided, including a torso belt configured to be secured around a torso of a patient, a forearm sling configured to support a forearm of the patient, and a lockable rotating platform. The lockable rotating platform includes a torso conforming element configured to be held against the torso of the patient by the torso belt, and a malleable semi-rigid supporting element. The torso conforming element includes a central portion and is curved along its length of extension between first and second ends to, thereby, conform to the torso of the patient. The malleable semi-rigid supporting element includes a rotation hub rotatably coupled to the central portion of the torso conforming element, a forearm platform operatively connected to the rotation hub, and a forearm support strut operatively connected between the rotation hub and a forearm support platform. Other orthoses and related methods are also provided.

29 Claims, 14 Drawing Sheets

(58) Field of Classification Search
CPC .......... A61F 5/373; A61F 5/3723; A61F 5/05; A61F 5/05858; A61F 2005/0167; A61F 2005/0151; A61F 2005/0158; A61F 2005/0179; A61F 2005/0153
USPC .............................................................. 602/1
See application file for complete search history.

(56) References Cited

U.S. PATENT DOCUMENTS

| | | | | |
|---|---|---|---|---|
| 5,385,536 | A * | 1/1995 | Burkhead | A61F 5/3753 602/5 |
| 6,932,781 | B2 | 8/2005 | Itoi | |
| 6,945,945 | B2 | 9/2005 | Givler et al. | |
| 7,074,202 | B1 | 7/2006 | Weber et al. | |
| 7,244,239 | B2 | 7/2007 | Howard | |
| 7,563,236 | B2 | 7/2009 | Kazmierczak et al. | |
| 7,771,332 | B1 * | 8/2010 | Al-Oboudi | A61F 5/3723 482/148 |
| 7,988,653 | B2 | 8/2011 | Fout et al. | |
| 8,287,478 | B2 | 10/2012 | Ostergard et al. | |
| 8,523,795 | B2 | 9/2013 | McCune et al. | |
| 8,591,441 | B2 | 11/2013 | Bonutti et al. | |
| 8,992,451 | B2 | 3/2015 | Fout | |
| 9,033,907 | B2 | 5/2015 | Noble | |
| 9,204,989 | B2 | 12/2015 | Begon et al. | |
| 9,320,635 | B2 | 4/2016 | Ex-Lubeskie et al. | |
| 9,498,369 | B2 | 11/2016 | Kilbey | |
| 9,572,702 | B2 | 2/2017 | Bonutti et al. | |
| 9,668,902 | B1 | 6/2017 | Krenzel | |
| 9,700,453 | B2 | 7/2017 | Benenati | |
| 9,918,864 | B2 | 3/2018 | Grant et al. | |
| 9,968,477 | B2 | 5/2018 | Lo | |
| 10,123,899 | B1 | 11/2018 | Theriot et al. | |
| 10,285,841 | B2 | 5/2019 | Pappady | |
| 10,327,942 | B2 | 6/2019 | Nolt et al. | |
| 10,420,670 | B2 | 9/2019 | Lemmon et al. | |
| 10,434,004 | B2 | 10/2019 | Nakamitsu | |
| 10,485,692 | B2 | 11/2019 | Kuorak et al. | |
| 10,507,130 | B1 | 12/2019 | Strasburger | |
| 10,603,201 | B2 | 3/2020 | Eriksson | |
| 10,610,400 | B1 | 4/2020 | Krenzel | |
| 10,660,780 | B1 | 5/2020 | Ostergard | |
| 10,736,767 | B2 | 8/2020 | Boileau et al. | |
| 10,772,782 | B2 | 9/2020 | Lebolt et al. | |
| 10,779,984 | B2 | 9/2020 | Bonutti et al. | |
| 10,786,384 | B2 | 9/2020 | Nakamitsu | |
| 10,792,178 | B2 | 10/2020 | Alvarez et al. | |
| 10,835,411 | B2 | 11/2020 | Sandwith | |
| 10,849,780 | B2 | 12/2020 | Cooper et al. | |
| 10,898,362 | B2 | 1/2021 | Bejarano | |
| 10,912,667 | B1 | 2/2021 | Sickles et al. | |
| 10,918,513 | B2 | 2/2021 | Golden et al. | |
| 10,966,853 | B2 | 4/2021 | Sotereanos et al. | |
| 11,058,569 | B2 | 7/2021 | Fair et al. | |
| 11,109,995 | B1 | 9/2021 | Anjonrin-Ohu et al. | |
| 11,179,265 | B2 | 11/2021 | Cox | |
| 11,207,202 | B2 | 12/2021 | Goldfarb et al. | |
| 11,234,851 | B2 | 2/2022 | Kaminsky et al. | |
| 11,234,855 | B2 | 2/2022 | Lemmon et al. | |
| 11,517,465 | B2 | 12/2022 | Boileau et al. | |
| 11,547,587 | B2 | 1/2023 | Bejarano | |
| 2003/0135141 | A1 | 7/2003 | Berhorst | |
| 2006/0167395 | A1 | 7/2006 | Sawa | |
| 2008/0228118 | A1 | 9/2008 | Bull et al. | |
| 2010/0229874 | A1 | 9/2010 | Branch | |
| 2011/0021962 | A1 | 1/2011 | Sorrenti | |
| 2011/0046529 | A1 | 2/2011 | Vollbrecht et al. | |
| 2012/0022421 | A1 | 1/2012 | Matthias | |
| 2012/0101420 | A1 | 4/2012 | Albrecht et al. | |
| 2012/0101421 | A1 | 4/2012 | Albrecht | |
| 2013/0190670 | A1 | 7/2013 | Von Zieglauer | |
| 2014/0305442 | A1 | 10/2014 | Bergenudd et al. | |
| 2014/0371644 | A1 | 12/2014 | Erbe et al. | |
| 2016/0199212 | A1 | 7/2016 | Turconi et al. | |
| 2017/0049604 | A1 | 2/2017 | Kemp | |
| 2018/0250151 | A1 | 9/2018 | Kaminsky et al. | |
| 2019/0076284 | A1 | 3/2019 | Kwark et al. | |
| 2019/0117439 | A1 | 4/2019 | Wortman et al. | |
| 2019/0254910 | A1 | 8/2019 | Mizera et al. | |
| 2019/0350738 | A1 | 11/2019 | Webster et al. | |
| 2019/0365554 | A1 | 12/2019 | Davies-Sekle | |
| 2020/0016009 | A1 | 1/2020 | Colleran | |
| 2020/0078200 | A1 | 3/2020 | Hardt et al. | |
| 2020/0121489 | A1 | 4/2020 | Quigley et al. | |
| 2020/0253770 | A1 | 8/2020 | Doyle | |
| 2020/0306072 | A1 | 10/2020 | Carney et al. | |
| 2020/0323673 | A1 | 10/2020 | Stebbins | |
| 2020/0323724 | A1 | 10/2020 | Neubauer et al. | |
| 2020/0368057 | A1 | 11/2020 | Boileau et al. | |
| 2021/0085506 | A1 | 3/2021 | Wonnacott | |
| 2021/0106453 | A1 | 4/2021 | Goel | |
| 2021/0386577 | A1 | 12/2021 | Bleau et al. | |
| 2022/0031490 | A1 | 2/2022 | Matthews | |
| 2022/0226142 | A1 | 7/2022 | Lemmon et al. | |
| 2022/0287863 | A1 | 9/2022 | Kaminsky et al. | |
| 2022/0339019 | A1 | 10/2022 | Burton et al. | |
| 2022/0387208 | A1 | 12/2022 | Paik et al. | |
| 2023/0013131 | A1 | 1/2023 | Chan et al. | |

FOREIGN PATENT DOCUMENTS

| | | | |
|---|---|---|---|
| CN | 203988531 | U | 12/2014 |
| CN | 209347357 | U | 9/2016 |
| CN | 206120525 | U | 4/2017 |
| CN | 206120526 | U | 4/2017 |
| CN | 206120527 | U | 4/2017 |
| CN | 106667644 | B | 5/2017 |
| CN | 206630741 | U | 11/2017 |
| CN | 107510529 | B | 12/2017 |
| CN | 208573872 | U | 12/2017 |
| CN | 107789111 | A | 3/2018 |
| CN | 108309537 | A | 7/2018 |
| CN | 108451693 | A | 8/2018 |
| CN | 108478317 | A | 9/2018 |
| CN | 108618877 | A | 10/2018 |
| CN | 109330757 | B | 2/2019 |
| CN | 208464380 | U | 2/2019 |
| CN | 208625956 | U | 3/2019 |
| CN | 208710202 | U | 4/2019 |
| CN | 208725986 | U | 4/2019 |
| CN | 208756287 | U | 4/2019 |
| CN | 209004373 | U | 6/2019 |
| CN | 209091798 | U | 7/2019 |
| CN | 209172634 | U | 7/2019 |
| CN | 209285883 | U | 8/2019 |
| CN | 110236760 | A | 9/2019 |
| CN | 209629928 | U | 11/2019 |
| CN | 209629930 | U | 11/2019 |
| CN | 209645171 | U | 11/2019 |
| CN | 110613544 | A | 12/2019 |
| CN | 209734263 | U | 12/2019 |
| CN | 209933119 | U | 1/2020 |
| CN | 209966708 | U | 1/2020 |
| CN | 110859695 | A | 3/2020 |
| CN | 210277433 | U | 4/2020 |
| CN | 111214318 | A | 6/2020 |
| CN | 210812305 | U | 6/2020 |
| CN | 111358613 | A | 7/2020 |
| CN | 210962537 | U | 7/2020 |
| CN | 211300567 | U | 8/2020 |
| CN | 211325975 | U | 8/2020 |
| CN | 211356128 | U * | 8/2020 |
| CN | 211409593 | U | 9/2020 |
| CN | 211409597 | U | 9/2020 |
| CN | 211704965 | U | 10/2020 |
| CN | 112022479 | A | 12/2020 |
| CN | 112137788 | B | 12/2020 |
| CN | 212066959 | U | 12/2020 |
| CN | 212261650 | U | 1/2021 |
| CN | 212547302 | U | 2/2021 |
| CN | 212547303 | U | 2/2021 |
| CN | 212662060 | U | 3/2021 |
| CN | 212699261 | U | 3/2021 |
| CN | 212754421 | U | 3/2021 |

(56) References Cited

FOREIGN PATENT DOCUMENTS

| | | | |
|---|---|---|---|
| CN | 112618138 | A | 4/2021 |
| CN | 112716676 | A | 4/2021 |
| CN | 212879723 | U | 4/2021 |
| CN | 212940110 | U | 4/2021 |
| CN | 213030981 | U | 4/2021 |
| CN | 213047550 | U | 4/2021 |
| CN | 213076148 | U | 4/2021 |
| CN | 112826648 | A | 5/2021 |
| CN | 113143567 | A | 7/2021 |
| CN | 113521673 | A | 10/2021 |
| CN | 214549774 | U | 11/2021 |
| CN | 214857923 | U | 11/2021 |
| CN | 214967419 | U | 12/2021 |
| CN | 215021460 | U | 12/2021 |
| CN | 215228985 | U | 12/2021 |
| CN | 215307206 | U | 12/2021 |
| CN | 215459108 | U | 1/2022 |
| CN | 215584527 | U | 1/2022 |
| CN | 215839790 | U | 2/2022 |
| EP | 1334705 | B1 | 8/2003 |
| EP | 1645251 | A2 | 4/2006 |
| EP | 1870062 | A1 | 12/2007 |
| EP | 2022450 | B1 | 2/2009 |
| EP | 2591757 | B1 | 5/2013 |
| EP | 2779964 | B1 | 9/2014 |
| EP | 2874579 | B1 | 5/2015 |
| EP | 3034052 | B1 | 6/2016 |
| EP | 3892242 | A1 | 10/2021 |
| FR | 2905261 | B1 | 3/2008 |
| FR | 2947718 | B1 | 1/2011 |
| FR | 2948282 | A1 | 1/2011 |
| IN | 201711024048 | A | 1/2019 |
| JP | 4566582 | B2 | 10/2010 |
| JP | 2017047149 | A | 3/2017 |
| JP | 6376930 | B2 | 8/2018 |
| JP | 2019154520 | A | 9/2019 |
| JP | 69780128 | B2 | 12/2021 |
| KR | 100883324 | B1 | 2/2009 |
| KR | 101031453 | B1 | 4/2011 |
| KR | 200465621 | Y1 | 3/2013 |
| KR | 200473627 | Y1 | 7/2014 |
| KR | 101666206 | B1 | 10/2016 |
| KR | 101785190 | B1 | 10/2017 |
| KR | 101858400 | B1 | 5/2018 |
| KR | 101860677 | B1 | 5/2018 |
| KR | 101891752 | B1 | 8/2018 |
| KR | 20190031696 | A | 3/2019 |
| KR | 20190054632 | A | 5/2019 |
| KR | 102243807 | B1 | 4/2021 |
| KR | 102302280 | B1 | 9/2021 |
| KR | 102326818 | B1 | 11/2021 |
| KR | 20220008111 | A | 1/2022 |
| KR | 102363066 | B1 | 2/2022 |
| KR | 20220018251 | A | 2/2022 |
| WO | 2008020254 | A1 | 2/2008 |
| WO | 2011086315 | A1 | 7/2011 |
| WO | 2019020960 | A1 | 1/2019 |
| WO | 2020229885 | A1 | 11/2020 |
| WO | 2020234077 | A1 | 11/2020 |
| WO | 2020263033 | A1 | 12/2020 |
| WO | 2021032795 | A1 | 2/2021 |
| WO | 2021063186 | A1 | 4/2021 |
| WO | 2021081173 | A1 | 4/2021 |
| WO | 2021093919 | A2 | 5/2021 |
| WO | 2025029937 | A1 | 2/2025 |

OTHER PUBLICATIONS

International Search Report and Written Opinion mailed on Nov. 4, 2024 in PCT/US2024/040414.

"Adjustable Shoulder brace and Arm Sling With Free Angle Metal Bar Customized Manufacturer, hand Shoulder brace arm slings ar . . . ", Global Sources Sourcing Sites, Mar. 2, 2022, 3:32 PM, https://www.globalsources.com/Arm-sling/Shoulder-Arm-Sling-Immobilizer-Braces-1170871566p.htm.

Brzóska, R et al. 360° Around Shoulder Instability, Springer, ISBN: 978-3-662-61074-9.

Chen P, Yang SJ, Wu H, et al. Design and clinical application of a combined shoulder abduction orthosis for post-burn treatment[J]. Chin J Burns, 2021, 37(1): 76-78. DOI: 10.3760/cma.j.cn501120-20200116-00027.

Isabella Fusaro, Stefania Orsini, Teresa Sforza, Roberto Rotini, Maria Grazia Benedetti, The use of braces in the rehabilitation treatmentof the post-traumatic elbow, Joints 2014;2(2):81-86, Physical Medicine and Rehabilitation Unit, Rizzoli Orthopaedic Institute, Via G. C. Pupilli 1, 40136 Bologna, Italy.

Kesner, S.B., L. Jentoft, F.L. Hammond, R.D. Howe, and M. Popovic. 2011. "Design Considerations for an Active Soft Orthotic System for Shoulder Rehabilitation." Annual International Conference of the IEEE Engineering in Medicine and Biology Society, Boston, MA, Aug. 30-Sep. 3, 2011: 9130-8134.

Ki Un Jang1, Ji Soo Choi2, Jeong Hyeon Mun2, Jong Hyun Jeon2, Cheong Hoon Seo2 and Jong Hyeon Kim3, Multi-axis shoulder abduction splint in acute burn rehabilitation: a randomized controlled pilot trial, Clinical Rehabilitation 2015, vol. 29(5) 439-446 © The Author(s) 2014.

Mcfarland EG, Curl LA, Urquhart MW, Kellam K. The sling Shoulder immobilization devices. Orthop Nurs. Jul.-Aug. 1997;16(4):17-20. PMID: 9287812.

OberHealth, Ober Abduction Immobilization Shoulder Brace 0 ° -120 °—Ober Health, Mar. 2, 2022, 3:30 PM, https://www.oberhealth.com/product/shoulder-abductor-fixator-medical-shoulder-dislocation-humerus-fracture-fixation-with-shoulder-abductor-orthosis/.

Ofer Levy, MD, MCh(Orth), FRCS, Thoracoscapular Fusion for Winging of the Scapula with Screw Fixation for Fascioscapulohumeral Dystrophy (Modified Copeland-Howard Procedure), pp. 1-13, J Bone Joint Surg Am. Aug. 7, 2013:95(15):1404-8.

RehabMart.Com, Tools for the job of living, 2025, ARYSE Adjustable Elevation Shoulder Brace, https://www.rehabmart.com/product/adjustable-elevation-shoulder-brace-47645.htm.

S. Erel et al., An adjustable shoulder abduction orthosis for the post-operative management of tendon transfers: A preliminary study, informa healthcare, Prosthetics and Orthotics International, Jun. 2008; 32(2): 129-135, Hacettepe University School of Physical Therapy and Rehabilitation, Samanpazari, Ankara, Turkey.

Schenk P, Bachmann E, Aichmair A, Götschi T, Gerber C, Meyer DC. Biomechanical and Clinical Evaluation of the Optimal Arm Position After Rotator Cuff Surgery With an Adjustable Abduction Brace. Orthopedics. 2021;44(1):e1-e6. doi:10.3928/01477447-20201210-01.

First Examination Report mailed on Feb. 6, 2026 in AU 2024315279.

IPRP mailed on Feb. 12, 2026 in WO PCT/US24/40414.

Foreign Office Action mailed on May 14, 2026 in CA 3300104.

Notice of Acceptance mailed on Jun. 1, 2026 in AU 2024315279.

* cited by examiner

ROTATING PLATFORM RIGID SHOULDER ORTHOSIS AND RELATED METHODS

RELATED APPLICATIONS

This application claims priority to U.S. Provisional Patent Application No. 63/530,218, filed Aug. 1, 2023, the contents of which is hereby incorporated by reference in their entirety.

FIELD OF THE INVENTION

The present disclosure relates, generally, to rotating platform rigid shoulder orthoses and related methods.

BACKGROUND OF THE INVENTION

Shoulder orthoses exist that aid in the stability or recovery of a shoulder injury that requires the shoulder joint and associated anatomy to be positioned in a desired orientation to promote healing, reduce discomfort during recovery, reduce forces on ligaments and affected and/or repaired muscles, and reduce forces and/or weight on the shoulder joint. These shoulder orthoses usually require the use of a shoulder sling that encapsulates the arm with the aim of limiting the mobility of the arm, and in-turn the shoulder joint, and reducing the weight or forces on the affected limb. Additionally, based on the type of injury and/or repair, the medical practitioner may want to implement a protocol where a desired position of the arm and shoulder would best increase healing and comfort during the healing process.

However, current brace offerings can be difficult or cumbersome to adjust. Accordingly, there remains a need for improved rotating platform rigid shoulder orthoses and related methods.

SUMMARY OF THE INVENTION

In some embodiments, an orthosis is provided. The orthosis includes a torso belt configured to be secured around a torso of a patient, a forearm sling configured to support a forearm of the patient, and a lockable rotating platform. The lockable rotating platform includes a torso conforming element configured to be held against the torso of the patient by the torso belt. The torso conforming element includes a central portion, a first end, and a second end. The torso conforming element is curved along its length of extension between the first end and the second end to, thereby, conform to the torso of the patient. The lockable rotating platform includes a malleable semi-rigid supporting element. The malleable semi-rigid supporting element includes a rotation hub rotatably coupled to the central portion of the torso conforming element. The malleable semi-rigid supporting element includes a forearm platform operatively connected to the rotation hub. The malleable semi-rigid supporting element includes a forearm support strut operatively connected between the rotation hub and a forearm support platform.

In some such embodiments, the orthosis is a shoulder brace. In some such embodiments, the torso conforming element and the malleable semi-rigid supporting element each comprise a malleable metal. In some embodiments, the rotation hub is rotatably coupled to the central portion of the torso conforming element about an axis that extends normal to a surface of the central portion. In some embodiments, the malleable semi-rigid supporting element comprises a first adjoining portion coupled to and extending away from the rotation hub to become a first curved portion, the first curved portion extending to become the forearm platform. In some embodiments, the malleable semi-rigid supporting element comprises a second adjoining portion coupled to and extending away from the rotation hub in an opposite direction of the first adjoining portion, the second adjoining portion extending to become a second curved portion, the second curved portion extending to become the forearm support strut, the forearm support strut extending to become a third curved portion, and the third curved portion extending to become the forearm support platform. In some embodiments, the forearm support strut and the forearm support platform are a monolithic, unitary component. In some embodiments, at least one of the first adjoining portion and the second adjoining portion extends away from the rotation hub in a same plane in which the rotation hub lies.

In some such embodiments, the orthosis includes a shoulder belt configured to be secured to the forearm sling and configured to be secured against a contralateral shoulder of the user.

In some such embodiments, the torso conforming element is sufficiently malleable to be bent into the precise curvature required to conform to the torso of the patient along a length of extension of torso conforming elements between the first end and the second end. In some such embodiments, the torso conforming element has a substantially constant width along a length of extension between the first end and the second end. In some such embodiments, the torso conforming element has a substantially constant thickness along a length of extension between the first end and the second end. In some such embodiments, corners of at least one of the first end and the second end of the torso conforming element have a radius of curvature sufficiently large to prevent the corners from poking into the torso of the patient while wearing the orthosis.

In some such embodiments, the rotation hub of the malleable semi-rigid supporting element is substantially planar and disposed parallel to the central portion of the torso conforming element. In some such embodiments, the central portion of the torso conforming element comprises a protruding pin and wherein the rotation hub comprises a plurality of detents, each configured to receive the protruding pin when the rotation hub is disposed in a respective lockable rotational orientation with respect to the torso conforming element to, thereby, lock the rotation hub of the malleable semi-rigid supporting element in a desired one of the lockable rotational orientations with respect to the central portion of the torso conforming element.

In some such embodiments, the forearm platform is planar such that a difference in orientation between a plane in which the first adjoining portion extends and a plane in which the forearm platform extends is directly determined by an amount of curvature induced in the intervening first curved portion. In some such embodiments, the first curved portion is configured to be bent to a desired degree sufficient to dispose the forearm platform in a desired orientation. In some such embodiments, the first curved portion is curved in a single dimension such that the curved portion does not possess compound curvature and such that the first curved portion is substantially flat along a direction perpendicular to the single dimension of curvature. In some such embodiments, the forearm support strut is planar such that a difference in orientation between a plane in which the second adjoining portion extends and a plane in which the forearm support strut extends is directly determined by an amount of curvature induced in the intervening second curved portion. In some such embodiments, the forearm support platform is planar such that a difference in orientation between a plane in which the forearm support strut extends and a plane in which the forearm support platform extends is directly determined by an amount of curvature induced in the intervening third curved portion. In some such embodiments, the forearm support strut extends from the second curved portion to an underside of the forearm platform, and the forearm support platform is disposed against and in parallel with the underside of the forearm platform. In some such embodiments, the second curved portion and the third curved portion are each curved in a single dimension such that the second curved portion and the third curved portion do not possess compound curvature and such that the second curved portion and the third curved portion are each substantially flat along a direction perpendicular to the single dimension of curvature.

In some such embodiments, the malleable semi-rigid supporting element comprises a single, monolithic element having a substantially constant width along its length of extension between a distal end of the forearm platform and a distal end of the forearm support platform. In some such embodiments, the malleable semi-rigid supporting element has a substantially constant thickness along its length of extension between a distal end of the forearm platform and a distal end of the forearm support platform. In some such embodiments, corners of a distal end of the forearm platform have a radius of curvature sufficiently large to prevent the corners from poking into the forearm of the patient while wearing the orthosis.

In some such embodiments, the lockable rotating platform further comprises an additional malleable member rotatably coupled, at a proximal portion thereof, to a distal portion of the forearm platform such that the additional malleable member is configured to rotate about an axis normal to a surface of the forearm platform. In some such embodiments, the additional malleable member is sufficiently malleable, and configured to be bent to a desired shape.

In some embodiments, the forearm support strut includes a first portion, and a second portion configured to slide with respect to the first portion and to adjustably lock or fixate in any one of a plurality of continuous or incremental extended configurations with respect to the first portion, the second portion extending to become a curved portion, which extends to become the forearm support platform.

In some embodiments, a method of using an orthosis is provided. The method includes securing a torso belt of the orthosis around a torso of a patient such that the torso belt holds a torso conforming element of a lockable rotating platform of the orthosis against the torso of the patient, wherein the torso conforming element includes a central portion, a first end, and a second end. The torso conforming element is curved along its length of extension between the first end and the second end to, thereby, conform to the torso of the patient. The method includes rotating a malleable semi-rigid supporting element of the lockable rotating platform relative to the torso conforming element to achieve a desired orientation of the malleable semi-rigid supporting element with respect to the torso conforming element, at least a portion of the malleable semi-rigid supporting element being incorporated into the torso belt. The malleable semi-rigid supporting element includes a rotation hub rotatably coupled to the central portion of the torso conforming element, a forearm platform operatively connected to the rotation hub, and a forearm support strut operatively connected between the rotation hub and a forearm support platform. The method includes inducing a first bend in the malleable semi-rigid supporting element sufficient to position the forearm platform in a desired orientation and inducing a second bend in the malleable semi-rigid supporting element sufficient to position the forearm support platform in contact with an underside of the forearm platform. The method includes supporting a forearm of the patient in a forearm sling of the orthosis on a top surface of the forearm platform such that the forearm is supported in a desired degree of internal or external rotation and a desired degree of adduction or abduction.

In some such embodiments, the orthosis is a shoulder brace. In some such embodiments, the torso conforming element and the malleable semi-rigid supporting element each comprise a malleable metal. In some embodiments, the rotation hub is rotatably coupled to the central portion of the torso conforming element about an axis that extends normal to a surface of the central portion. In some embodiments, the malleable semi-rigid supporting element comprises a first adjoining portion coupled to and extending away from the rotation hub to become a first curved portion, the first curved portion, formed by the inducing of the first ben din the malleable semi-rigid supporting element, the first curved portion extending to become the forearm platform. In some embodiments, the malleable semi-rigid supporting element comprises a second adjoining portion coupled to and extending away from the rotation hub in an opposite direction of the first adjoining portion, the second adjoining portion extending to become a second curved portion, formed by the inducing of the second bend in the malleable semi-rigid element, the second curved portion extending to become the forearm support strut, the forearm support strut extending to become a third curved portion, and the third curved portion extending to become the forearm support platform. In some embodiments, the forearm support strut and the forearm support platform are a monolithic, unitary component. In some embodiments, at least one of the first adjoining portion and the second adjoining portion extends away from the rotation hub in a same plane in which the rotation hub lies.

In some such embodiments, the method further includes securing a shoulder belt to the forearm sling and against a contralateral shoulder of the user.

In some such embodiments, the torso conforming element is sufficiently malleable to be bent into the precise curvature required to conform to the torso of the patient along a length of extension of torso conforming elements between the first end and the second end. In some such embodiments, the torso conforming element has a substantially constant width along a length of extension between the first end and the second end. In some such embodiments, the torso conforming element has a substantially constant thickness along a length of extension between the first end and the second end. In some such embodiments, corners of at least one of the first end and the second end of the torso conforming element have a radius of curvature sufficiently large to prevent the corners from poking into the torso of the patient while wearing the orthosis.

In some such embodiments, the rotation hub of the malleable semi-rigid supporting element is substantially planar and disposed parallel to the central portion of the torso conforming element. In some such embodiments, the central portion of the torso conforming element comprises a protruding pin and wherein the rotation hub comprises a plurality of detents, each configured to receive the protruding pin when the rotation hub is disposed in a respective lockable rotational orientation with respect to the torso conforming element to, thereby, lock the rotation hub of the malleable semi-rigid supporting element in a desired one of the lockable rotational orientations with respect to the central portion of the torso conforming element.

In some such embodiments, the forearm platform is planar such that a difference in orientation between a plane in which the first adjoining portion extends and a plane in which the forearm platform extends is directly determined by an amount of curvature induced in the intervening first curved portion. In some such embodiments, the first curved portion is curved in a single dimension such that the curved portion does not possess compound curvature and such that the first curved portion is substantially flat along a direction perpendicular to the single dimension of curvature. In some such embodiments, the forearm support strut is planar such that a difference in orientation between a plane in which the second adjoining portion extends and a plane in which the forearm support strut extends is directly determined by an amount of curvature induced in the intervening second curved portion. In some such embodiments, the forearm support platform is planar such that a difference in orientation between a plane in which the forearm support strut extends and a plane in which the forearm support platform extends is directly determined by an amount of curvature induced in the intervening third curved portion. In some such embodiments, the forearm support strut extends from the second curved portion to the underside of the forearm platform, and the forearm support platform is disposed against and in parallel with the underside of the forearm platform. In some such embodiments, the second curved portion and the third curved portion are each curved in a single dimension such that the second curved portion and the third curved portion do not possess compound curvature and such that the second curved portion and the third curved portion are each substantially flat along a direction perpendicular to the single dimension of curvature.

In some such embodiments, the malleable semi-rigid supporting element comprises a single, monolithic element having a substantially constant width along its length of extension between a distal end of the forearm platform and a distal end of the forearm support platform. In some such embodiments, the malleable semi-rigid supporting element has a substantially constant thickness along its length of extension between a distal end of the forearm platform and a distal end of the forearm support platform. In some such embodiments, corners of a distal end of the forearm platform have a radius of curvature sufficiently large to prevent the corners from poking into the forearm of the patient while wearing the orthosis.

In some such embodiments, the lockable rotating platform further comprises an additional malleable member rotatably coupled, at a proximal portion thereof, to a distal portion of the forearm platform, and the method further comprises rotating the additional malleable member about an axis normal to a surface of the forearm platform to achieve a desired orientation of the additional malleable with respect to the forearm platform. In some such embodiments, the additional malleable member is sufficiently malleable and configured to be bent to a desired shape.

In some embodiments, the forearm support strut includes a first portion, and a second portion configured to slide with respect to the first portion and to adjustably lock or fixate in any one of a plurality of continuous or incremental extended configurations with respect to the first portion, the second portion extending to become a curved portion, which extends to become the forearm support platform.

In some embodiments, a method of manufacturing an orthosis is provided. The method includes providing a torso belt of the orthosis configured to be secured around a torso of a patient. The method includes providing a forearm sling of the orthosis configured to support a forearm of the patient. The method includes assembling a lockable rotating platform of the orthosis. The lockable rotating platform including a torso conforming element configured to be held against the torso of the patient by the torso belt. The torso conforming element including a central portion, a first end, and a second end, wherein the torso conforming element is curved along its length of extension between the first end and the second end to, thereby, conform to the torso of the patient. The method includes coupling a rotation hub of a malleable semi-rigid supporting element to the central portion of the torso conforming element. The malleable semi-rigid supporting element further includes a forearm platform operatively connected to the rotation hub. The malleable semi-rigid supporting element further includes a forearm support strut connected between the rotation hub and a forearm support platform.

In some such embodiments, the orthosis is a shoulder brace. In some such embodiments, the torso conforming element and the malleable semi-rigid supporting element each includes a malleable metal. In some embodiments, the rotation hub is rotatably coupled to the central portion of the torso conforming element about an axis that extends normal to a surface of the central portion. In some embodiments, the malleable semi-rigid supporting element comprises a first adjoining portion coupled to and extending away from the rotation hub to become a first curved portion, the first curved portion extending to become the forearm platform. In some embodiments, the malleable semi-rigid supporting element comprises a second adjoining portion coupled to and extending away from the rotation hub in an opposite direction of the first adjoining portion, the second adjoining portion extending to become a second curved portion, the second curved portion extending to become the forearm support strut, the forearm support strut extending to become a third curved portion, and the third curved portion extending to become the forearm support platform. In some embodiments, the forearm support strut and the forearm support platform are a monolithic, unitary component. In some embodiments, at least one of the first adjoining portion and the second adjoining portion extends away from the rotation hub in a same plane in which the rotation hub lies.

In some such embodiments, the method further includes providing a shoulder belt configured to be secured to the forearm sling and configured to be secured against a contralateral shoulder of the user.

In some such embodiments, the torso conforming element is sufficiently malleable to be bent into the precise curvature required to conform to the torso of the patient along a length of extension of torso conforming elements between the first end and the second end. In some such embodiments, the torso conforming element has a substantially constant width along a length of extension between the first end and the second end. In some such embodiments, the torso conforming element has a substantially constant thickness along a length of extension between the first end and the second end. In some such embodiments, corners of at least one of the first end and the second end of the torso conforming element are formed to have a radius of curvature sufficiently large to prevent the corners from poking into the torso of the patient while wearing the orthosis.

In some such embodiments, the rotation hub of the malleable semi-rigid supporting element is substantially planar and disposed parallel to the central portion of the torso conforming element. In some such embodiments, the central portion of the torso conforming element comprises a protruding pin and wherein the rotation hub comprises a plurality of detents, each configured to receive the protruding pin when the rotation hub is disposed in a respective lockable rotational orientation with respect to the torso conforming element to, thereby, lock the rotation hub of the malleable semi-rigid supporting element in a desired one of the lockable rotational orientations with respect to the central portion of the torso conforming element.

In some such embodiments, the forearm platform is planar such that a difference in orientation between a plane in which the first adjoining portion extends and a plane in which the forearm platform extends is directly determined by an amount of curvature induced in the intervening first curved portion. In some such embodiments, the first curved portion is configured to be bent to a desired degree sufficient to dispose the forearm platform in a desired orientation. In some such embodiments, the first curved portion is curved in a single dimension such that the curved portion does not possess compound curvature and such that the first curved portion is substantially flat along a direction perpendicular to the single dimension of curvature. In some such embodiments, the forearm support strut is planar such that a difference in orientation between a plane in which the second adjoining portion extends and a plane in which the forearm support strut extends is directly determined by an amount of curvature induced in the intervening second curved portion. In some such embodiments, the forearm support platform is planar such that a difference in orientation between a plane in which the forearm support strut extends and a plane in which the forearm support platform extends is directly determined by an amount of curvature induced in the intervening third curved portion. In some such embodiments, the forearm support strut extends from the second curved portion to an underside of the forearm platform, and the forearm support platform is disposed against and in parallel with the underside of the forearm platform. In some such embodiments, the second curved portion and the third curved portion are each curved in a single dimension such that the second curved portion and the third curved portion do not possess compound curvature and such that the second curved portion and the third curved portion are each substantially flat along a direction perpendicular to the single dimension of curvature.

In some such embodiments, the malleable semi-rigid supporting element comprises a single, monolithic element having a substantially constant width along its length of extension between a distal end of the forearm platform and a distal end of the forearm support platform. In some such embodiments, the malleable semi-rigid supporting element has a substantially constant thickness along its length of extension between a distal end of the forearm platform and a distal end of the forearm support platform. In some such embodiments, corners of a distal end of the forearm platform have a radius of curvature sufficiently large to prevent the corners from poking into the forearm of the patient while wearing the orthosis.

In some such embodiments, the method includes rotatably coupling an additional malleable member, at a proximal portion thereof, to a distal portion of the forearm platform such that the additional malleable member is configured to rotate about an axis normal to a surface of the forearm platform. In some embodiments, the additional malleable member is sufficiently malleable, and configured, to be bent to a desired shape.

In some embodiments, the forearm support strut includes a first portion, and a second portion configured to slide with respect to the first portion and to adjustably lock or fixate in any one of a plurality of continuous or incremental extended configurations with respect to the first portion, the second portion extending to become a curved portion, which extends to become the forearm support platform.

In some embodiments, yet another orthosis is provided. The orthosis includes a torso belt configured to be secured around a torso of a patient. The orthosis includes a forearm sling configured to support a forearm of the patient. The orthosis includes a lockable rotating platform. The lockable rotating platform includes a torso conforming element configured to be held against the torso of the patient by the torso belt. The torso conforming element includes a central portion, a first end, and a second end, wherein the torso conforming element is curved along its length of extension between the first end and the second end to, thereby, conform to the torso of the patient. The lockable rotating platform includes a malleable semi-rigid supporting element. The malleable semi-rigid supporting element includes a rotation hub rotatably coupled to the central portion of the torso conforming element. The malleable semi-rigid supporting element includes a forearm platform operatively connected to the rotation hub. The malleable semi-rigid supporting element includes a telescoping forearm support strut coupled between the rotation hub and a forearm support platform of the malleable semi-rigid supporting element or between the rotation hub and the forearm platform.

In some embodiments, the malleable semi-rigid supporting element includes a first portion of the telescoping forearm support strut pivotally coupled to the rotation hub by a first hinge, and a second portion of the forearm support strut pivotally coupled to the forearm platform by a second hinge, wherein the first portion is configured to slide, extend, or otherwise telescope with respect to the second portion and to adjustably lock or fixate in any one of a plurality of continuous or incremental extended and/or telescoped configurations with respect to the second portion.

DETAILED DESCRIPTION

Embodiments of this disclosure relate to rotating platform rigid shoulder orthoses and related methods.

Example Terminology

Figure 1:
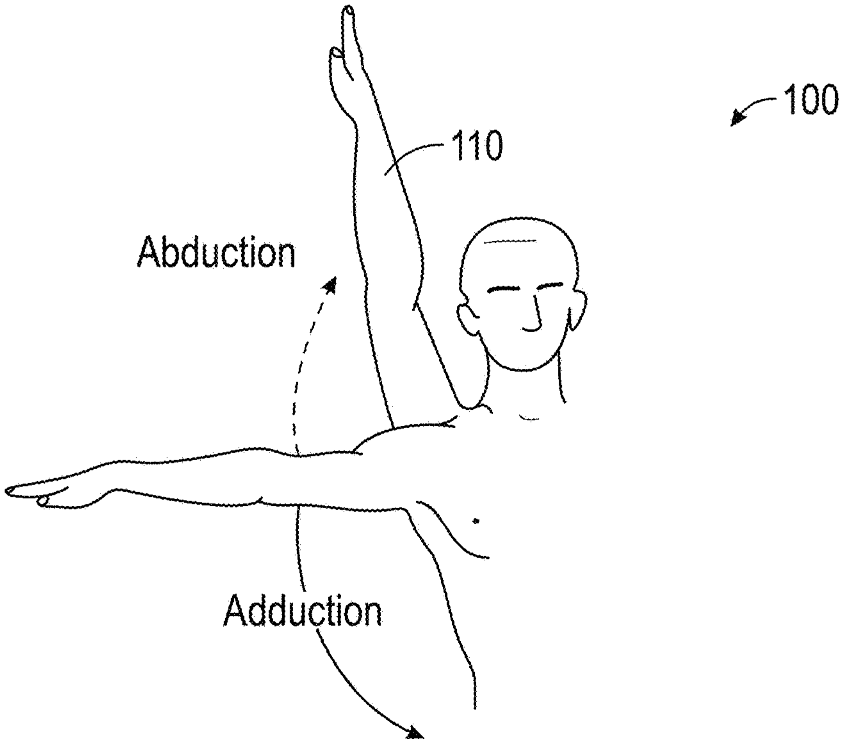
FIG. 1 illustrates a patient's arm disposed in positions of varying abduction and/or adduction.
Figure 2:
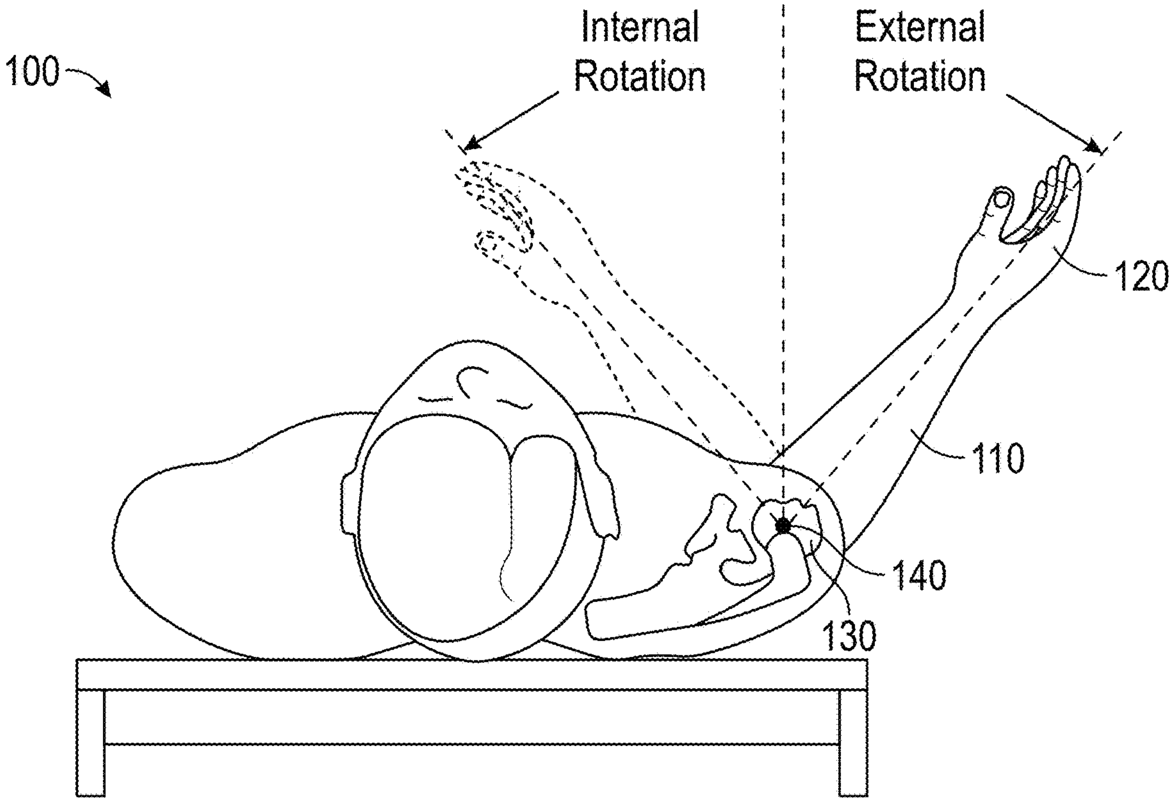
FIG. 2 illustrates a top-down view of a patient's arm disposed in positions of varying internal and/or external rotation.

The complex movement of the human shoulder joint can be broken down into two simple movements for purposes of developing an orthosis to position the arm effectively. FIG. 1 illustrates the opposing orientations of abduction and adduction for an arm 110 of a human 100, while FIG. 2 illustrates the opposing orientations of internal rotation and external rotation of arm 110 of human 100. For example, as illustrated in FIG. 1, abduction of the arm represents movement of the arm away from the midline of the body. Conversely, adduction of the arm represents the opposite, or movement of the arm towards the midline of the body. And as illustrated in FIG. 2, internal rotation (IR) represents rotation of the humerus 130 about its longitudinal axis 140 such that the hand 120 moves towards the midline of the body while arm 110 is flexed to, for example, 90° at the elbow. External rotation (ER) describes external rotation of humerus 130 around its longitudinal axis 140. For both IR and ER, the degree of rotation may be dependent on the degree of abduction at the shoulder.

Figure 3:
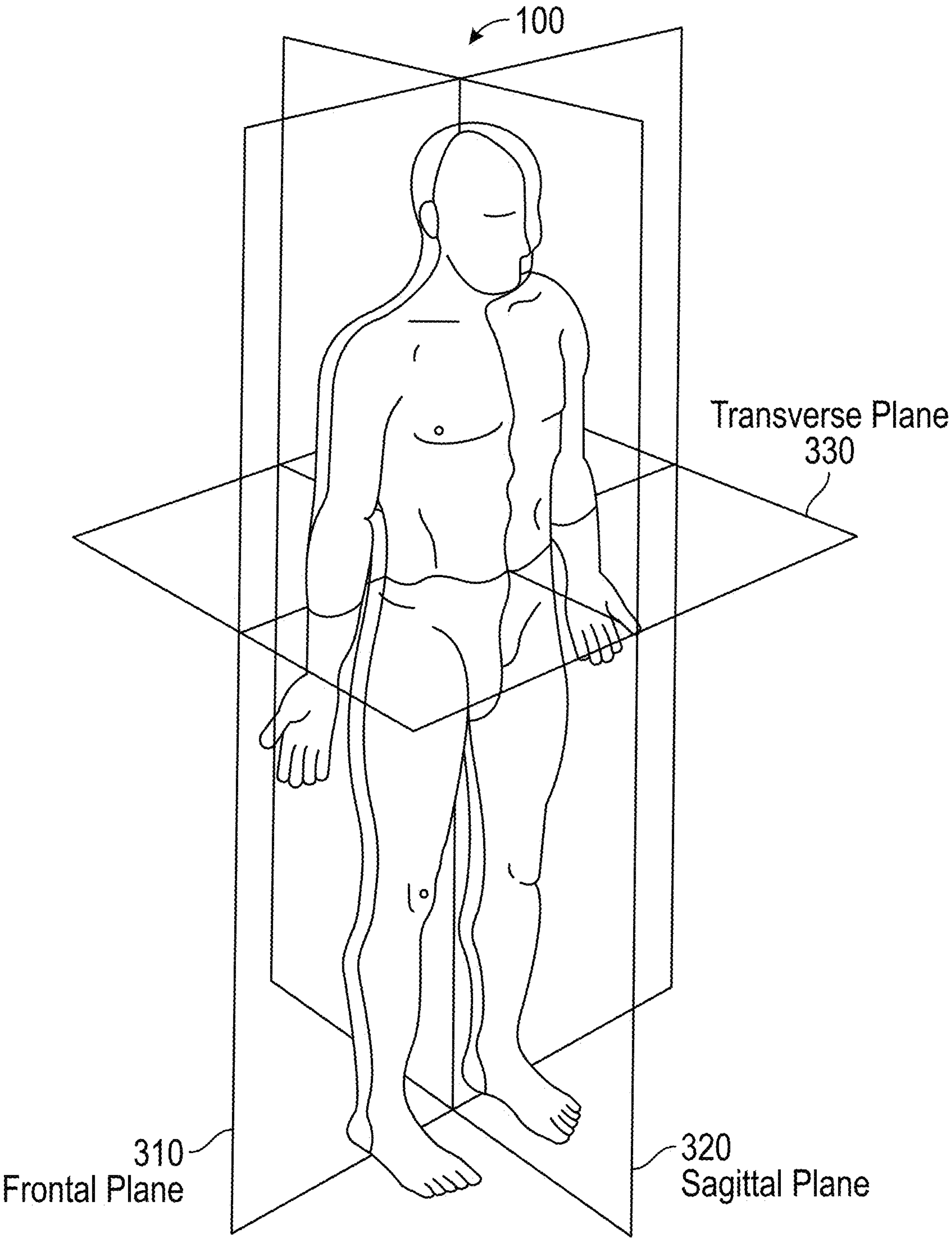
FIG. 3 illustrates a perspective view of orthogonal frontal, sagittal and transverse planes of a patient's body.

Furthermore, several body planes are identified in FIG. 3, which may be utilized to define fixed and/or adjustable orientation(s) of one or more features or elements of any shoulder orthosis herein with respect to the human body 100 to which such shoulder orthoses are attached.

When a person is standing vertically, the frontal plane (or coronal plane) 310 is illustrated as a vertical plane running from side to side that divides body 100, or any of its parts, into anterior and posterior portions. Frontal plane 310 is orthogonal (or perpendicularly oriented) with respect to both the sagittal plane 320 and the transverse plane 330.

When a person is standing vertically, sagittal plane 320 is illustrated as a vertical plane running anterior-posterior and divides body 100, or any of its parts, into left and right portions. Sagittal plane 320 is orthogonal (or perpendicularly oriented) with respect to both frontal plane 310 and transverse plane 330.

When a person is standing vertically, transverse plane 330 is illustrated as a horizontal plane running anterior-posterior and divides body 100 into upper (superior) and lower (inferior) portions. Transverse plane 330 is orthogonal (or perpendicularly oriented) with respect to both frontal plane 310 and sagittal plane 320.

Discussion of Orthoses

Figure 4:
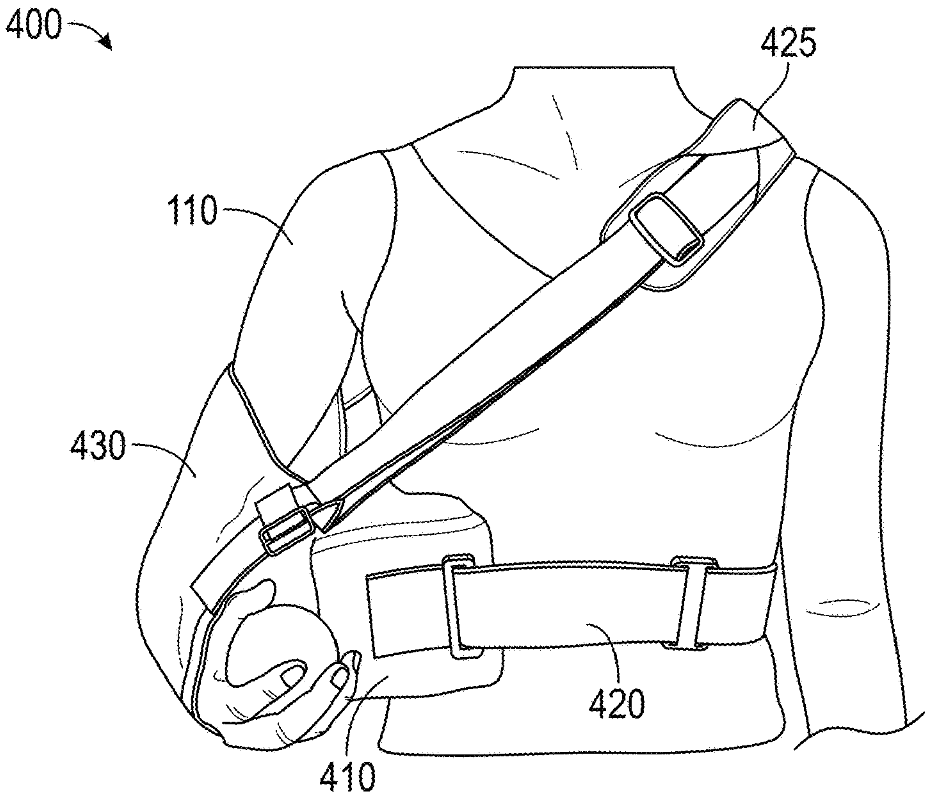
FIG. 4 illustrates a shoulder brace including a torso belt, a shoulder belt, a forearm sling and an abduction pillow, according to some example embodiments.
Figure 5:
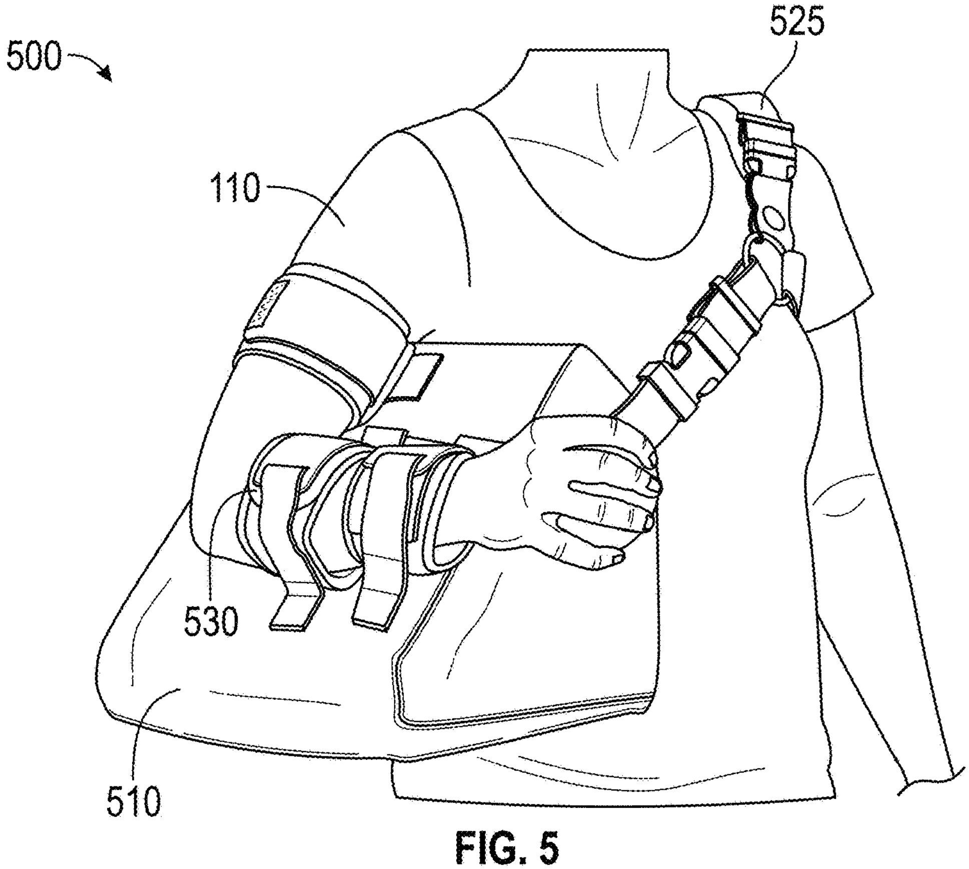
FIG. 5 illustrates a shoulder brace including a shoulder belt, a forearm sling and an abduction pillow, according to some example embodiments.

According to some examples, as shown in FIGS. 4 and 5, higher angles of abduction (e.g., 90 degrees of abduction such that the humerus is oriented substantially horizontal when the user is standing vertically) can only be achieved with the use of add-on devices, such as frame modifiers or abduction pillows (see, e.g., orthosis 400 of FIG. 4 utilizing an abduction pillow 410 coupled to removable belt 420 and arm sling 430 coupled to a shoulder belt 425, and orthosis 500 of FIG. 5 utilizing an abduction pillow 510 coupled to shoulder belt 525 and arm sling 530 coupled to abduction pillow 510).

Figure 6:
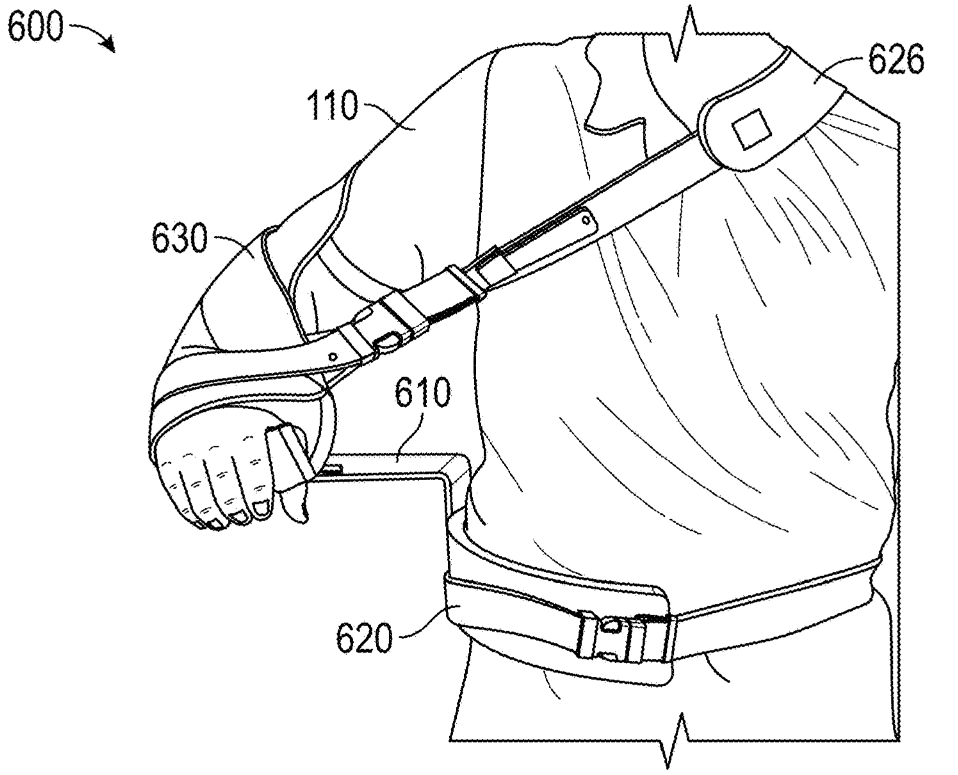
FIG. 6 illustrates a shoulder brace including a rigid malleable frame disposed between a torso belt and a forearm sling, according to some example embodiments.
Figure 7:
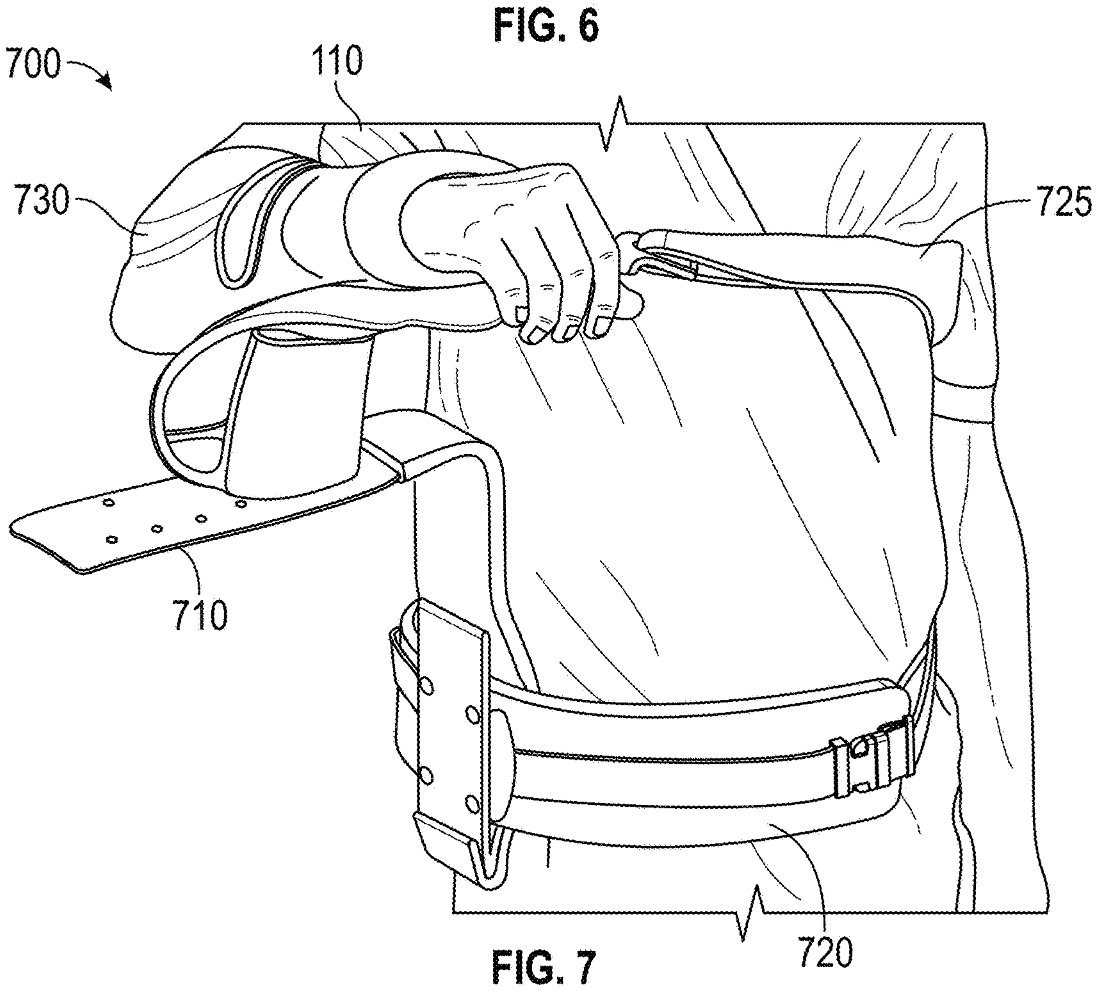
FIG. 7 illustrates a shoulder brace including a bolt-on secondary piece disposed between a torso belt and a forearm sling, according to some example embodiments.

Current shoulder orthoses having a rigid element to provide internal rotation (IR) or external rotation (ER) of the arm during recovery do not have a simple method to induce larger degrees of arm abduction angles (up to 90 degrees abduction) without the introduction of abduction pillows (e.g., as shown in FIGS. 4 and 5) or bolt-on secondary pieces 710 requiring time to disassemble/reassemble into a retrofitted product (see, e.g., orthosis 700 of FIG. 7 illustrating secondary piece 710 coupled to waist belt 720, secondary piece 710 coupled to arm sling 730, and arm sling 730 further coupled to shoulder belt 725) or use of a much more complex brace structure with pivoting support (see, e.g., the Enovis™ Ultrasling Quadrant). As another example, orthoses 600 of FIG. 6 may utilize a rigid malleable frame 610 that is worn by the patient on their torso in the form of a removable belt 620, wherein malleable frame 610 is configured to be easily reshaped to provide a resting platform onto which the patient's arm sling 630 can be securely attached. The reshaping of platform 610 may provide the needed alignment to position arm 110 in internal or external rotation, however arm abduction is limited because of the constraints of the rigid frame elements.

Accordingly, embodiments of several orthoses, described below, may overcome one or more of the above-described deficiencies and/or other deficiencies of current orthoses.

Example Embodiments of Orthoses According to the Disclosure

Figure 8:
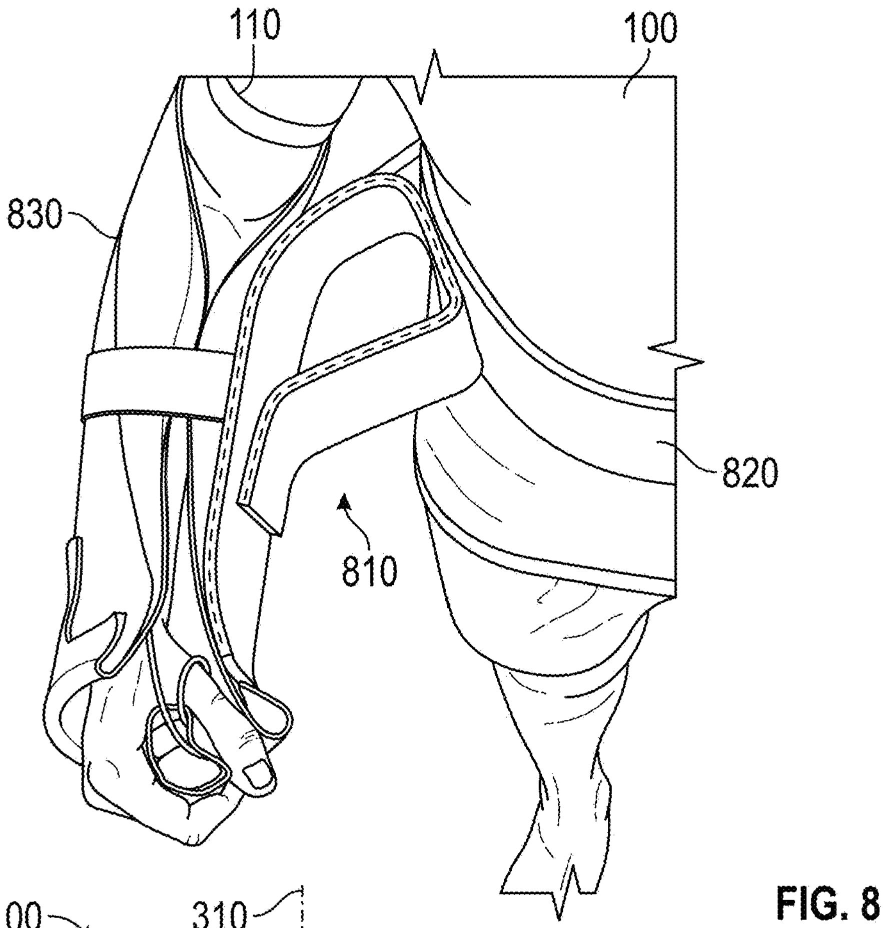
FIG. 8 illustrates a shoulder orthosis including a lockable rotating platform having semi-rigid elements that may be bent into a desirable form, according to some example embodiments.

This disclosure introduces, at FIGS. 8-17, the concept of a shoulder orthosis 800 comprising a lockable rotating platform 810, where lockable rotating platform 810 comprises semi-rigid elements that may be bent into a desirable form, shape and/or orientation to transform the internal/external rotation frame structure into a more effective abduction device (see, e.g., the shape illustrated by the dotted lines in FIG. 8 and, further, equivalent and/or similar shapes shown in FIGS. 9-17). While several embodiments are described herein, similar bending and/or malleability to that described herein may also or alternatively be accomplished through the use of rigid members incorporating mechanical hinges or plastic living hinges. As will be described in more detail below, lockable rotating platform 810 is rotatable in relation to a torso belt 820 such that the semi-rigid, malleable elements of lockable rotating platform 810 can be repositioned to create a more stable platform for the arm 110 of the patient while providing the desired degrees of IR/ER and/or adduction/abduction of arm 110.

Figure 9:
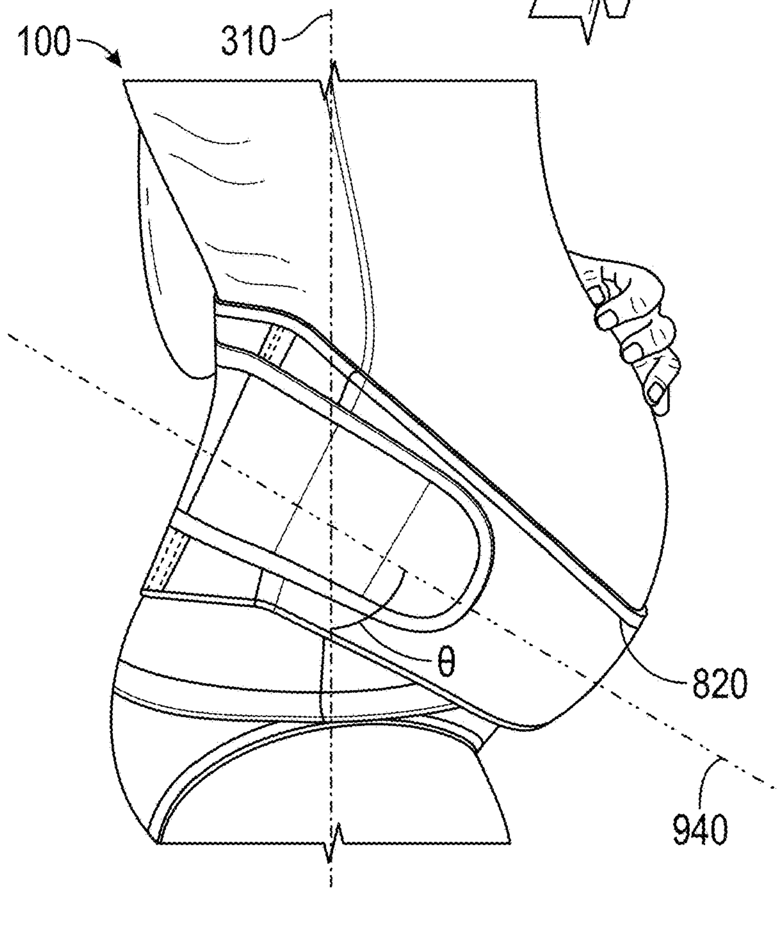
FIG. 9 illustrates a side view of a non-right angle between a path of extension of a torso belt of the shoulder orthosis of FIG. 8 and the frontal plane of the patient, according to some example embodiments.

As shown in FIG. 9, due to patient anatomy and/or stature, torso belt 820 (and associated rigid and/or semi-rigid portions of lockable rotating platform 810 that are integrated in, and/or with, torso belt 820 and that would extend along the line 940 in FIG. 9), may not always align perfectly parallel to transverse plane 330 of the body 100 (see, e.g., FIG. 3). As such, absent the ability to rotate lockable rotating platform 810 with respect to torso belt 820, the resting platform in either the IR/ER or abducted configurations may not have been capable of effectively providing the desired orientation to position arm 110. Accordingly, lockable rotating platform 810, by providing a plurality of indexed positioning locations for fixing the rotation of platform 810 with respect to torso belt 820, allows a medical practitioner to select a position that best appropriately aligns belt 820 and lockable rotating platform 810 for the anatomy of the patient. Additionally, in an effort to accommodate a universal-use device, and reduce the need to have limb specific orthosis available at medical institutions, lockable rotating platform 810 may be rotated by 180 degrees in either direction, thereby allowing a medical practitioner to utilize the orthosis 800 on either the right or left limb of the patient. Orthosis 800 will now be described in more detail in connection with FIGS. 8-16 below.

Figure 10:
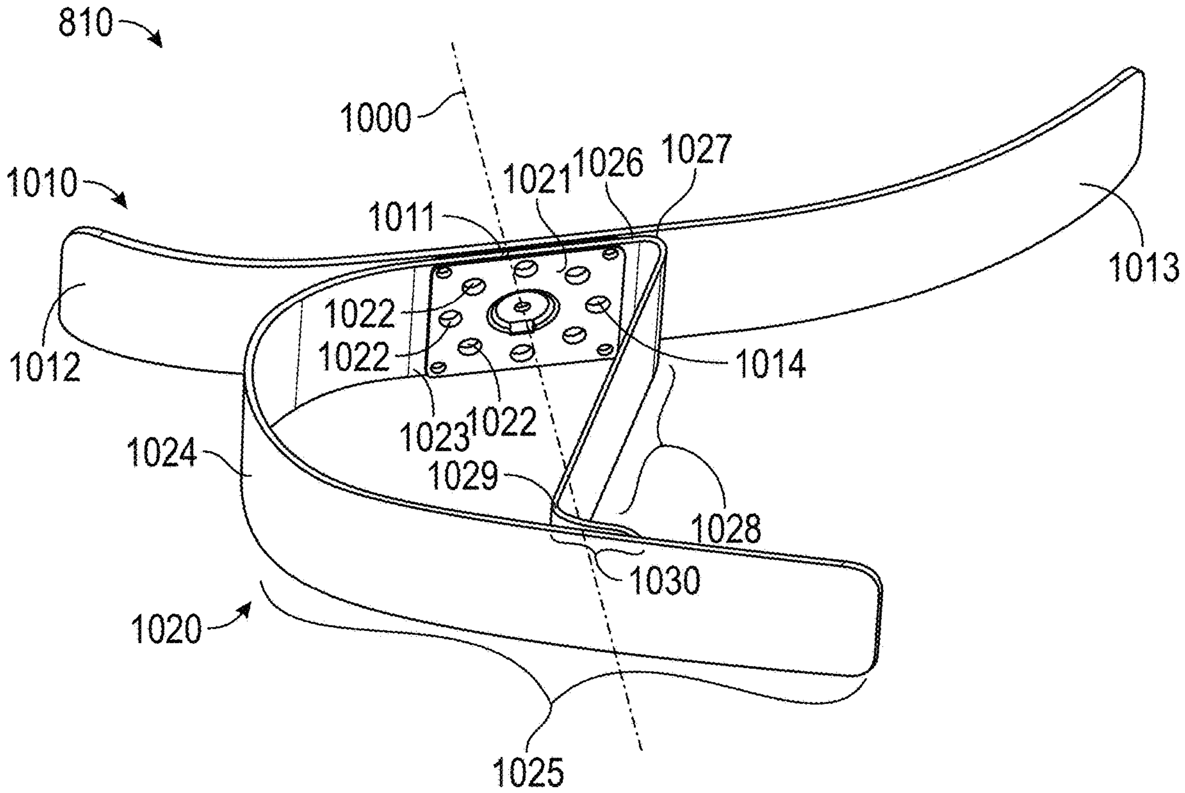
FIG. 10 illustrates a perspective view of a lockable rotating platform of the shoulder orthosis of FIG. 8, according to some example embodiments.
Figure 11:
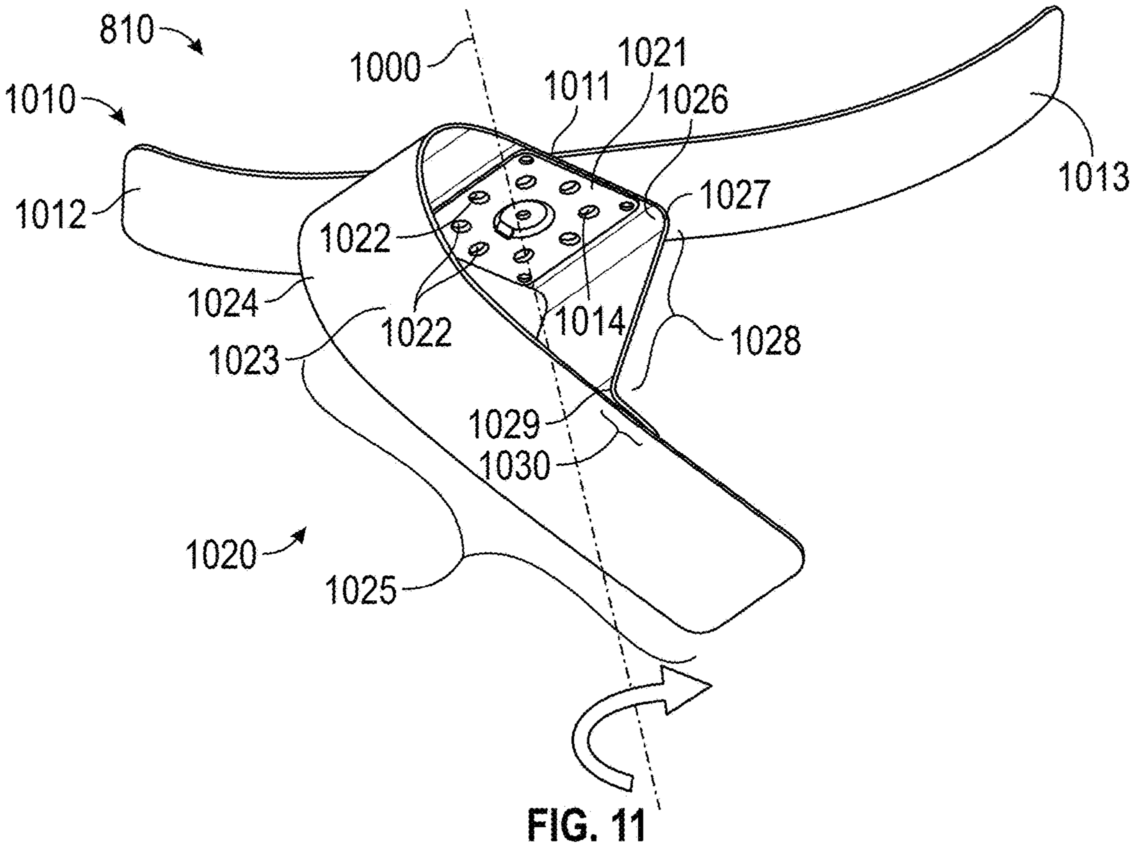
FIG. 11 illustrates a perspective view of the lockable rotating platform of FIG. 10 having a malleable semi-rigid supporting element thereof rotated with respect to a torso conforming element thereof, according to some example embodiments.
Figure 12:
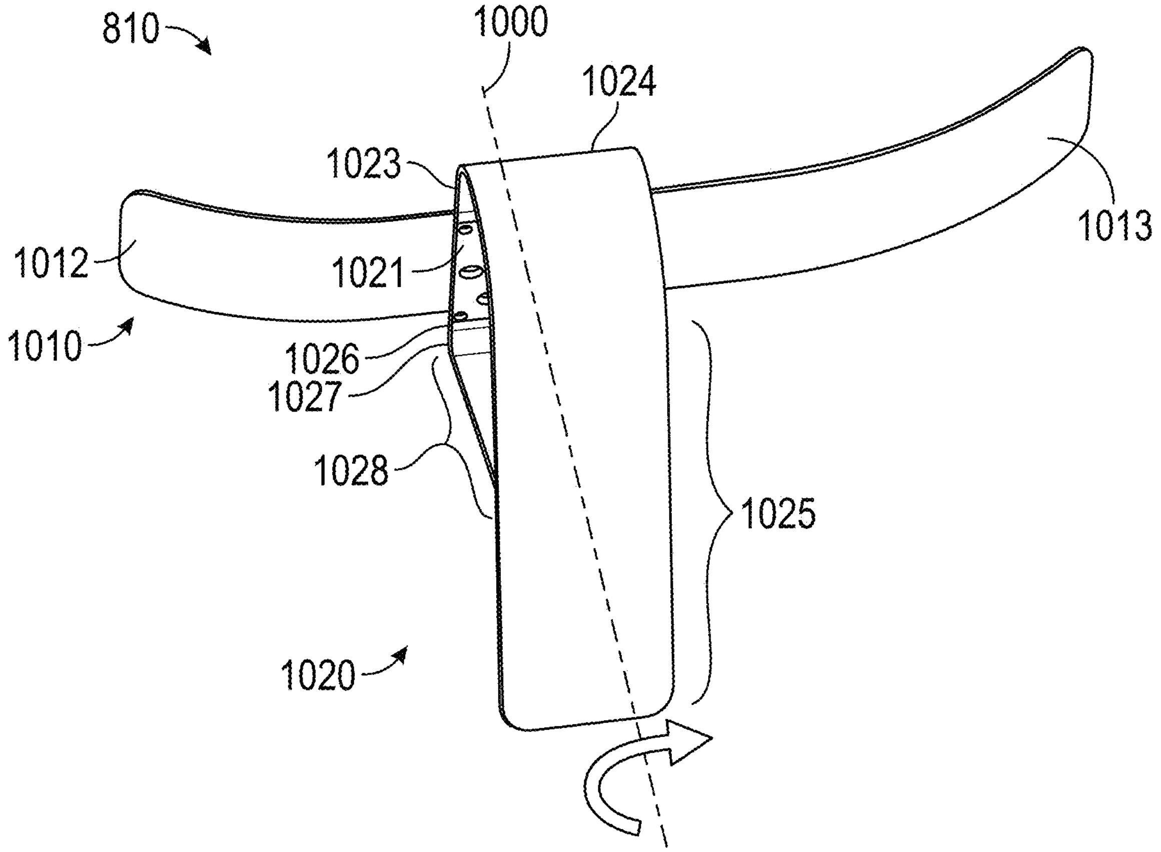
FIG. 12 illustrates a perspective view of the lockable rotating platform of FIG. 11 having the malleable semi-rigid supporting element further rotated with respect to the torso conforming element compared to FIG. 11, according to some example embodiments.

For example, turning to FIG. 10, orthosis 800 comprises lockable rotating platform 810. Platform 810 comprises a torso conforming element 1010, configured to be held (e.g., directly) against the side and/or torso of the user by torso belt 820, and a malleable semi-rigid supporting element 1020 rotatably coupled to a central portion 1011 of torso conforming element 1010. Malleable semi-rigid supporting element 1020 is sufficiently malleable that at least portions thereof are specifically configured to be bent into a desired orientation (e.g., under distorting pressure appropriately applied by a practitioner and/or the patient), yet rigid enough to hold that desired orientation (e.g., while loaded with forces and/or pressure(s) applied by a patient wearing orthosis 800) and, thereby, support the arm 110 of the patient in a desired degree of IR/ER and/or in a desired degree of adduction/abduction, as will be described in more detail below.

In some embodiments, at least a portion of torso conforming element 1010 is disposed within and/or encapsulated by a fabric, overmolded or injected plastic, and/or other external layer of orthosis 800 against which the patient's skin and/or clothing directly contact when orthosis 800 is worn (e.g., within torso belt 820 such that, when torso belt 820 is properly secured around the waist and/or torso of the user, torso conforming element 1010 is held (e.g., directly) against a substantially uninterrupted extent of the side and/or torso of the user by torso belt 820 between a first end 1012 and a second end 1013 of torso conforming element 1010). Accordingly, in some such embodiments, torso conforming element 1010 may be curved along its length of extension between first end 1012 and second end 1013 to, thereby, conform to the substantially uninterrupted extent of side and/or torso of the user. In some such embodiments, torso conforming element 1010 may be semi-rigid and sufficiently malleable to be bent into the precise curvature along its length of extension between first end 1012 and second end 1013 required to conform to the side and/or torso of the individual user of orthosis 800, but also sufficiently rigid to hold that conformal shape when orthosis 800 is worn by a patient. Accordingly, torso conforming element 1010 may comprise a metal, such as but not limited to aluminum, thin steels and/or stainless steel and/or resin plastic. In some embodiments, torso conforming element 1010 has a substantially constant width along its length of extension between first end 1012 and second end 1013. In some embodiments, torso conforming element 1010 has a substantially constant thickness along its length of extension between first end 1012 and second end 1013. In some embodiments, corners of first end 1012 and/or of second end 1013 may be rounded, e.g., having a predetermined radius of curvature that is sufficiently large to prevent those corners of first end 1012 and/or of second end 1013 from undesirably poking into the side and/or torso of the user while wearing orthosis 800, thereby, preventing pressure marks and/or contusions caused by inappropriate pressure points between the patient and of the orthosis.

Malleable semi-rigid supporting element 1020 comprises a rotation hub 1021 rotatably coupled to central portion 1011 of torso conforming element 1010. In some embodiments, rotation hub 1021 is substantially planar and disposed parallel to central portion 1011. Rotation hub 1021 is configured to rotate with respect to torso conforming element 1010 about axis 1000 (see, e.g., FIGS. 10-12). In some embodiments, rotation axis 1000 extends outwardly in a direction normal (i.e., perpendicular) to the surface of central portion 1011 through which rotation axis 1000 extends. In some embodiments, rotation hub 1021 is substantially planar. In some embodiments, rotation hub 1021 comprises a plurality of apertures and/or detents 1022, each configured to receive a protruding detent pin or element 1014 of central portion 1011 of torso conforming element 1010 when rotation hub 1021, and so malleable semi-rigid supporting element 1020, is disposed in a different lockable rotational orientation with respect to torso conforming element 1010. Accordingly, detent pin or element 1014 may be dislodged from one of apertures and/or detents 1022 and indexed into another of the apertures and/or detents 1022 to lock rotation hub 1021 of malleable semi-rigid supporting element 1020 in a desired rotational orientation with respect to central portion 1011 of torso conforming element 1010 (see, e.g., FIG. 12).

Malleable semi-rigid supporting element 1020 extends in opposite directions away from rotation hub 1021. In one direction, a first adjoining portion 1023 of supporting element 1020 is directly coupled to and/or integrally extends away from rotation hub 1021 in the same plane in which rotation hub 1021 lies. First adjoining portion 1023 extends continuously to become a first curved portion 1024. And first curved portion 1024 extends continuously to become forearm platform 1025. Accordingly, forearm platform 1025 is operatively connected to rotation hub 1021. In some embodiments, forearm platform 1025 is also planar such that a difference in orientation between a plane in which first adjoining portion 1023 extends and a plane in which forearm platform 1025 extends (and, so, the prescribed abduction angle of arm 110) is directly determined by the amount of curvature induced in intervening first curved portion 1024.

Figure 13:
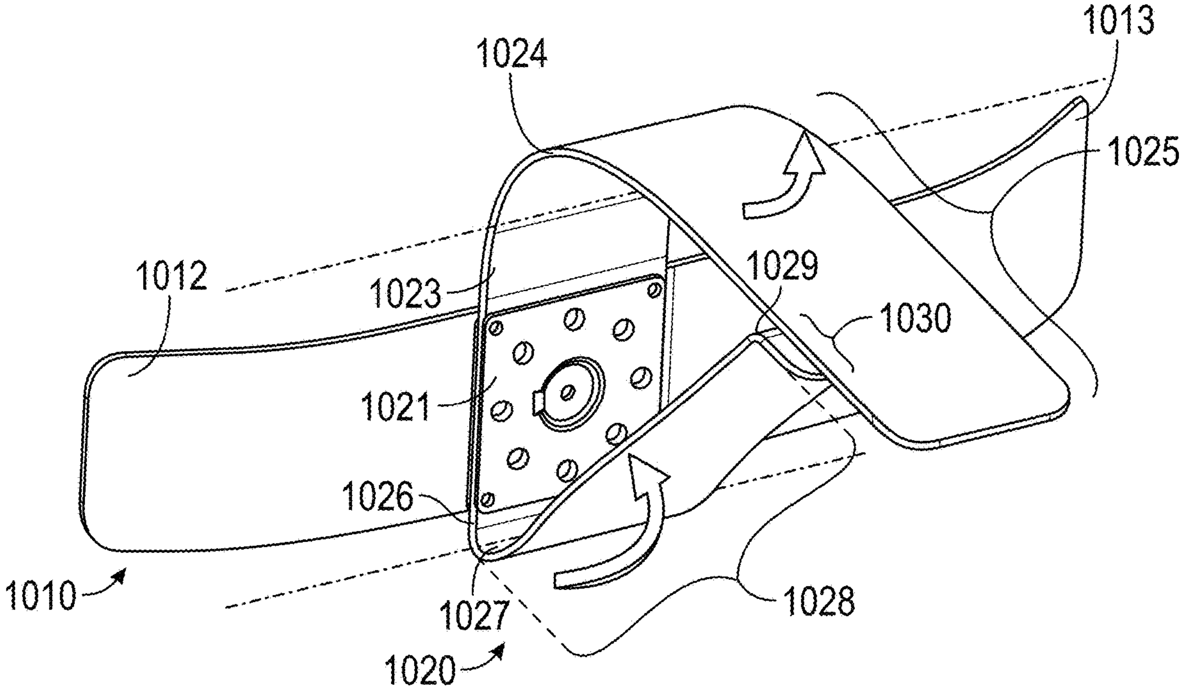
FIG. 13 illustrates a perspective view of the lockable rotating platform of FIG. 12 further having one or more portions of the malleable semi-rigid supporting element bent into desired orientations for holding a patient's arm in desired degrees of adduction or abduction and/or of internal or external rotation, according to some example embodiments.

Accordingly, once rotation hub 1021 of malleable semi-rigid supporting element 1020 is fixed in a desired rotational orientation with respect to central portion 1011 of torso conforming element 1010, a desired orientation of forearm platform 1025 can be achieved by bending first curved portion 1024 to a desired degree sufficient to dispose forearm platform 1025 in the desired orientation (see, e.g., FIG. 13). In some embodiments, first curved portion 1024 is continuously curved in a single dimension (e.g., does not possess compound curvature) such that first curved portion 1024 is substantially flat along a direction perpendicular to the single dimension of curvature.

Extending from rotation hub 1021 in the opposite direction from first adjoining portion 1023, a second adjoining portion 1026 of supporting element 1020 is directly coupled to and/or integrally extends away from rotation hub 1021 in the same plane in which rotation hub 1021 lies. Second adjoining portion 1026 extends continuously to become a second curved portion 1027. Second curved portion 1027 extends continuously to become forearm support strut 1028. Forearm support strut 1028 extends continuously to become third curved portion 1029. And third curved portion 1029 extends continuously to become forearm support platform 1030. Accordingly, forearm support strut 1028 is operatively connected between rotation hub 1024 and forearm support platform 1030. And, in some embodiments, forearm support strut 1028 and forearm support platform 1030 comprise a monolithic, unitary component. In some embodiments, forearm support strut 1028 is also planar such that a difference in orientation between a plane in which second adjoining portion 1026 extends and a plane in which forearm support strut 1028 extends is directly determined by the amount of curvature induced in intervening second curved portion 1027. In some embodiments, forearm support platform 1030 is also planar such that a difference in orientation between a plane in which forearm support strut 1028 extends and a plane in which forearm support platform 1030 extends is directly determined by the amount of curvature induced in intervening third curved portion 1029.

In some alternative embodiments, rather than extending from second adjoining portion 1026, forearm support platform 1030 may extend from a distal end of forearm platform 1025, there being a bend (not shown) therebetween. In some such embodiments, forearm support platform 1030, third bend 1029, forearm support strut 1028, a bend similar to, the same as, or opposite in direction from second bend 1027, and a feature similar to, the same as, or extending in an opposite direction from second adjoining portion 1026 may all be present. In some such embodiments, a terminating end (e.g., equivalent to second adjoining portion 1026 but being couplable and decouplable with and/or from rotation hub 1021) may be configured to rest on a ledge or in a groove (not shown) to, thereby, support forearm platform 1025 in a desired degree of IR/OR and/or adduction/abduction.

Accordingly, malleable semi-rigid supporting element 1020 may comprise a metal, such as but not limited to aluminum, thin steels and/or stainless steel and/or resin plastic. Accordingly, once rotation hub 1021 is fixed in a desired rotational orientation with respect to central portion 1011, and the desired orientation of forearm platform 1025 is achieved by bending first curved portion 1024, a desired amount of bending may be introduced into second curved portion 1027 such that forearm support strut 1028 extends from second curved portion 1027 to an underside of forearm platform 1025, and a desired amount of bending may be introduced into third curved portion 1029 such that forearm support platform 1030 is disposed against and in parallel with the underside of forearm platform 1025 (see, e.g., FIG. 13). In some embodiments, forearm support strut 1028 may be configured to extend at least in that, as the angle of abduction/adduction and/or internal/external rotation forearm platform 1025 changes, a length of malleable semi-rigid supporting element 1020 that forearm support strut 1028 comprises, e.g., the length between second curved portion 1027 and third curved portion 1029, is adjustable at least in that as the length of forearm support strut 1028 increases, third curved portion 1029 may and will be disposed a commensurately greater distance from second curved portion 1027, e.g., malleable semi-rigid supporting element 1020 is purposely bent to affect third curved portion 1029 at a position that will result in the suitable length of forearm support strut 1028. In some embodiments, second curved portion 1027 is continuously curved in a single dimension (e.g., does not possess compound curvature) such that second curved portion 1027 is substantially flat along a direction perpendicular to the single dimension of curvature. In some embodiments, third curved portion 1029 is continuously curved in a single dimension (e.g., does not possess compound curvature) such that third curved portion 1029 is substantially flat along a direction perpendicular to the single dimension of curvature.

In some embodiments, malleable semi-rigid supporting element 1020 is a single, monolithic element between the distal end of forearm platform 1025 and the distal end of 1030 forearm support platform. In some embodiments, malleable semi-rigid supporting element 1020 has a substantially constant width along its length of extension between the distal end of forearm platform 1025 and the distal end of 1030 forearm support platform. In some embodiments, malleable semi-rigid supporting element 1020 has a substantially constant thickness along its length of extension between the distal end of forearm platform 1025 and the distal end of 1030 forearm support platform. In some embodiments, corners of the distal end of forearm platform 1025 and the distal end of 1030 forearm support platform may be rounded, e.g., similar to or the same as the rounded corners of torso conforming element 1010. In some embodiments, all or at least a portion of malleable semi-rigid supporting element 1020 is disposed within and/or encapsulated by a fabric, overmolded or injected plastic, and/or other external layer of orthosis 800 against which the patient's skin and/or clothing directly contact when orthosis 800 is worn.

In some other embodiments, for example, as shown in at least FIGS. 14-18, to achieve relatively higher angles of abduction (e.g., angles above 45 degrees), it may be desirable to have the malleable element that provides support to platform 1025 be extendible. For example, by extending an element similar to forearm support strut 1028, a more stable structure may be achieved, upon which the weight of the arm can be fully supported. As will be described in connection with one or more figures below, such extension may be accomplished by having this member comprise a plurality of plates meant to slide, translate and/or telescope with respect to (e.g., in relationship to) each other to accommodate the desired length (see, e.g., FIGS. 14 and 15 below). Additionally, or alternatively, such extension may also occur by adding onto the original length of forearm support strut 1028 by means of a second member (e.g., members 1604, 1629 and/or 1630 as shown in at least FIG. 16) meant to be used specifically for these higher angles of abduction. Additionally, or alternatively, such extension may also occur by variable linear extension of lockable elements at desired lengths (e.g., first portion 1702 and second portion 1704 as a piston-cylinder combination, a wire cabling pulley system, or sets of springs as shown in at least FIGS. 17 and 18).

Figure 14:
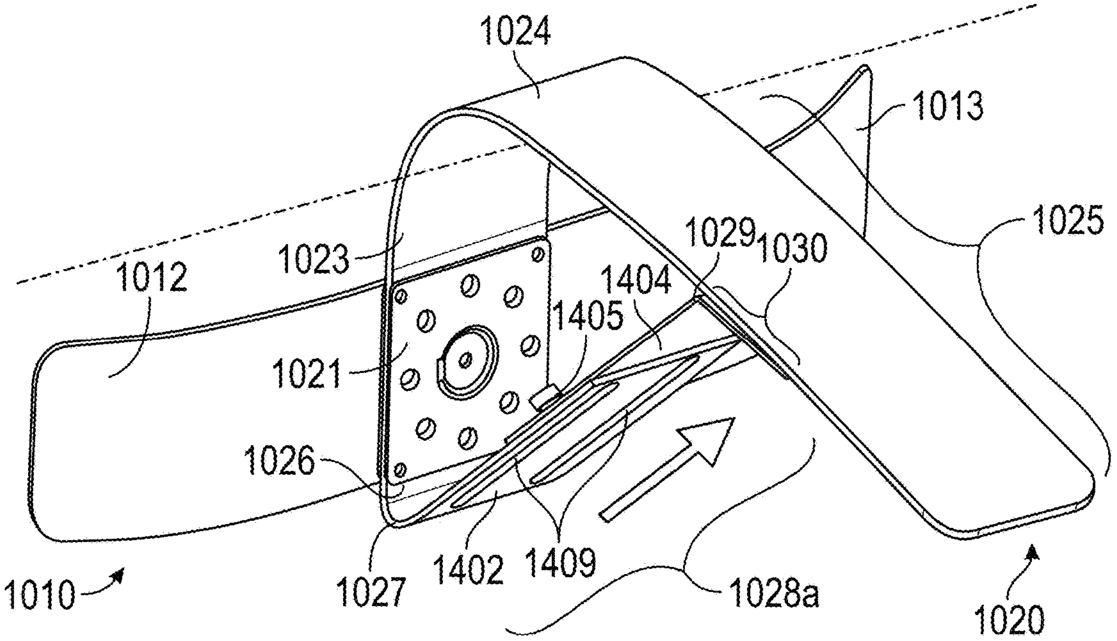
FIG. 14 illustrates a perspective view of another lockable rotating platform for holding a patient's arm in desired degrees of adduction or abduction and/or of internal or external rotation, according to some example embodiments.
Figure 15:
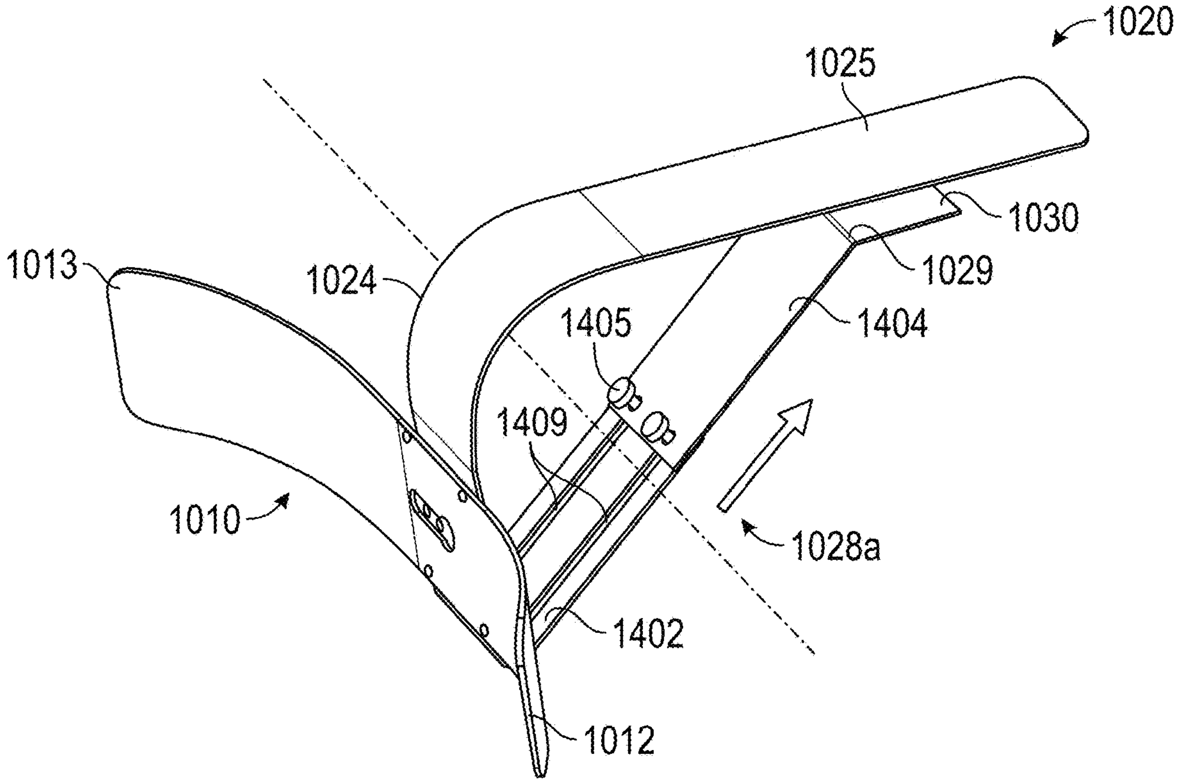
FIG. 15 illustrates another perspective view of the lockable rotating platform of FIG. 14, according to some example embodiments.

For example, in FIGS. 14 and 15, malleable semi-rigid supporting element 1020 comprises platform 1025, first curved portion 1024, first adjoining portion 1023, rotation hub 1021, second adjoining portion 1026 and second curved portion 1026 as previously described. However, in such embodiments, malleable semi-rigid supporting element 1020 may alternatively comprise a telescoping or extendable support strut 1028*a* in place of previously described forearm support strut 1028. Telescoping or extendable support strut 1028*a* is ultimately coupled between rotation hub 1021 and forearm support platform 1030, although telescoping or extendable support strut 1028*a* could alternatively be disposed between rotation hub 1021 and forearm support 1025 itself.

Telescoping or extendable support strut 1028*a* comprises a first portion 1402 configured to slide, extend, or otherwise telescope, with respect to a second portion 1404. First portion 1402 is configured to adjustably lock or adjustably fixate in any one of a plurality of continuous or incremental extended and/or telescoped configurations. For example, first portion 1402 is illustrated as comprising one or more slots 1409 extending parallel to a length of extension of first portion 1402 and second portion 1404 is illustrated as comprising a locking mechanism 1405, for example one or more thumb screws, or the like, each configured to extend through a respective one of slots 1409 and clamp or hold first portion 1402 against second portion 1404 at the desired degree of extension when sufficiently turned and/or otherwise tightened. In some embodiments, first portion 1402 may be substantially the same, or similar, to forearm support strut 1028, however, adding the one or more slots 1409 and omitting bend 1029 and support platform 1030; and second portion 1404 may be substantially the same, or similar, to forearm support 1028, however, adding locking mechanism 1405 and being coupled to, extending continuously to become, or otherwise including, bend 1029 and then support platform 1030.

Accordingly, a difference in orientation between a plane in which second rotation hub 1021 or adjoining portion 1026 extends and a plane in which telescoping or extending support strut 1028*a* extends is directly determined by the amount of curvature induced in intervening second curved portion 1027. And, in some embodiments, a difference in orientation between a plane in which telescoping and/or extending forearm support strut 1028*a* extends and a plane in which forearm support platform 1030 or forearm platform 1025 extends is directly determined by the amount of curvature induced in intervening third curved portion 1029.

Accordingly, once rotation hub 1021 is fixed in a desired rotational orientation with respect to central portion 1011 and the desired orientation of forearm platform 1025 is achieved by bending first curved portion 1024, a desired amount of bending may be introduced into second curved portion 1027 such that telescoping forearm support strut 1028*a*, comprising first portion 1402 and second portion 1404 held in place by locking mechanism 1405, extends to or toward an underside of forearm platform 1025, and a desired amount of bending may be introduced into third curved portion 1029 such that forearm support platform 1030 is disposed against and in parallel with the underside of forearm platform 1025 when forearm platform 1025 is disposed to provide the user's arm a desired amount of abduction or adduction and a desired amount of internal or external rotation.

Figure 16:
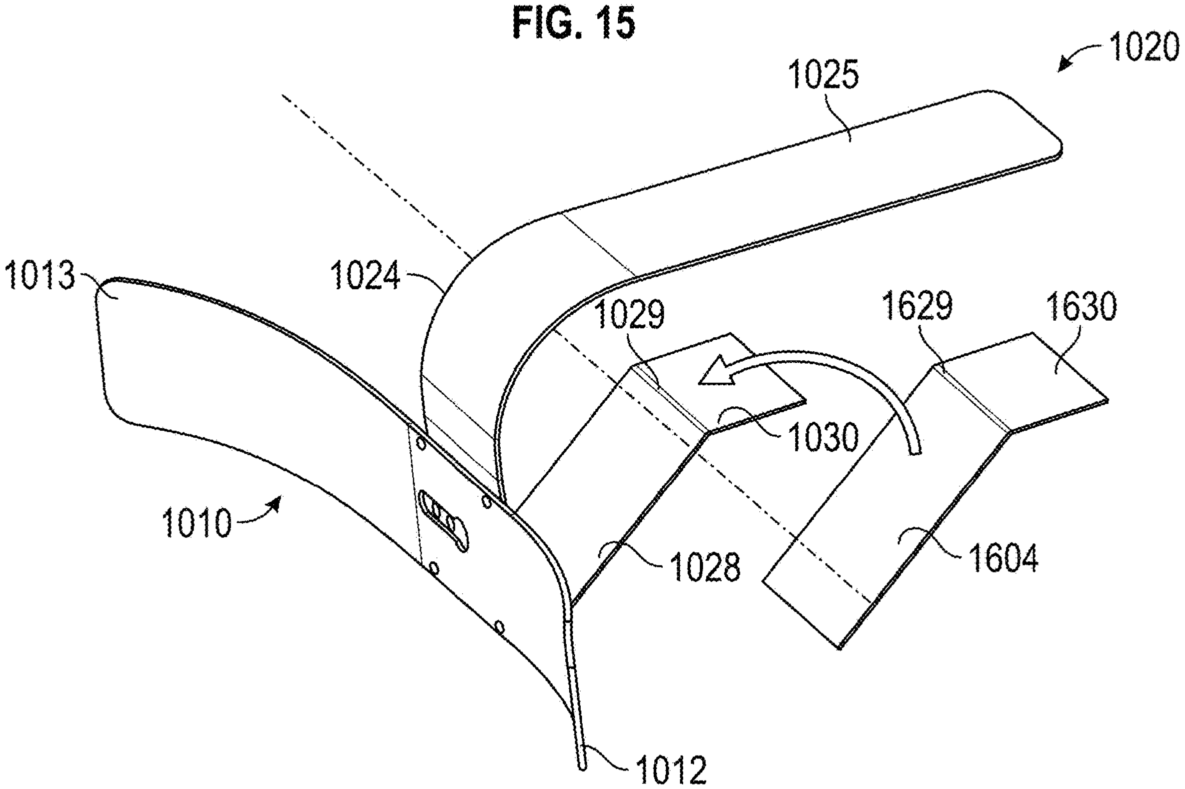
FIG. 16 illustrates a perspective view of yet another lockable rotating platform for holding a patient's arm in desired degrees of adduction or abduction and/or of internal or external rotation, according to some example embodiments.

In some other embodiments, for example, as shown in FIG. 16, malleable semi-rigid supporting element 1020 is substantially as previously described in connection with or as shown in at least FIG. 13, however, further comprising a forearm support strut extension 1604, which continuously extends to become a curved portion 1629, which continuously extends to become a forearm support strut extension platform 1630. Accordingly, forearm support strut extension 1604, curved portion 1629 and forearm support strut extension platform 1630 may be substantially the same, or similar, to forearm support strut 1028, third bent portion 1029 and support platform 1030, respectively, as previously described.

In operation, at least forearm support 1028, third bent portion 1029 and support platform 1030 may be covered in a hook and/or loop material. Similarly, at least a portion of forearm support strut extension 1604 and, in some embodiments, curved portion 1629 and/or forearm support strut extension platform 1630 are also covered in a complementary hook and/or loop material such that a desired length of extension of a support strut comprising support 1028 and extension 1604 may be obtained by placing forearm support strut extension 1604 against support strut 1028 with a desired degree of overlap and such that the hook and loop material couples forearm support strut extension 1604 against support strut 1028 along the entire length of the coupled hook and loop material. This also provides resistance to any torque between forearm support strut extension 1604 and support strut 1028 caused by the weight and/or movement of the user's arm on platform 1025 when platform 1630 is disposed against the underside thereof.

Accordingly, a difference in orientation between a plane in which extension support strut 1604 extends and a plane in which forearm support platform 1630 or forearm platform 1025 extends is directly determined by the amount of curvature induced in intervening curved portion 1629.

Figure 17:
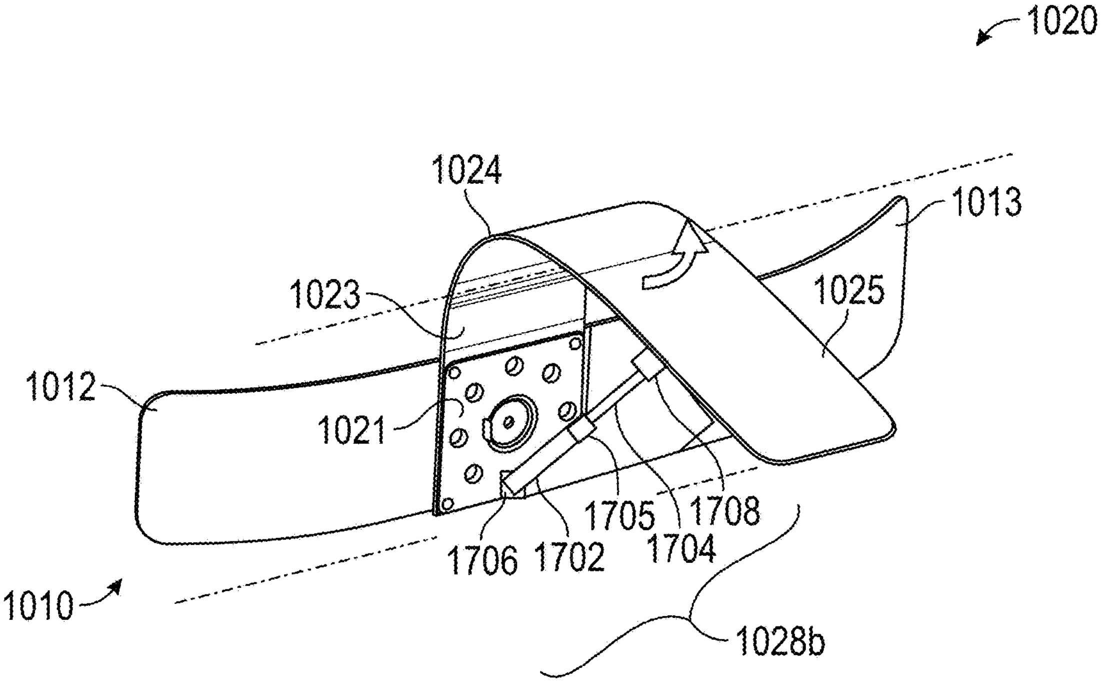
FIG. 17 illustrates a perspective view of yet another lockable rotating platform for holding a patient's arm in desired degrees of adduction or abduction and/or of internal or external rotation, according to some example embodiments.
Figure 18:
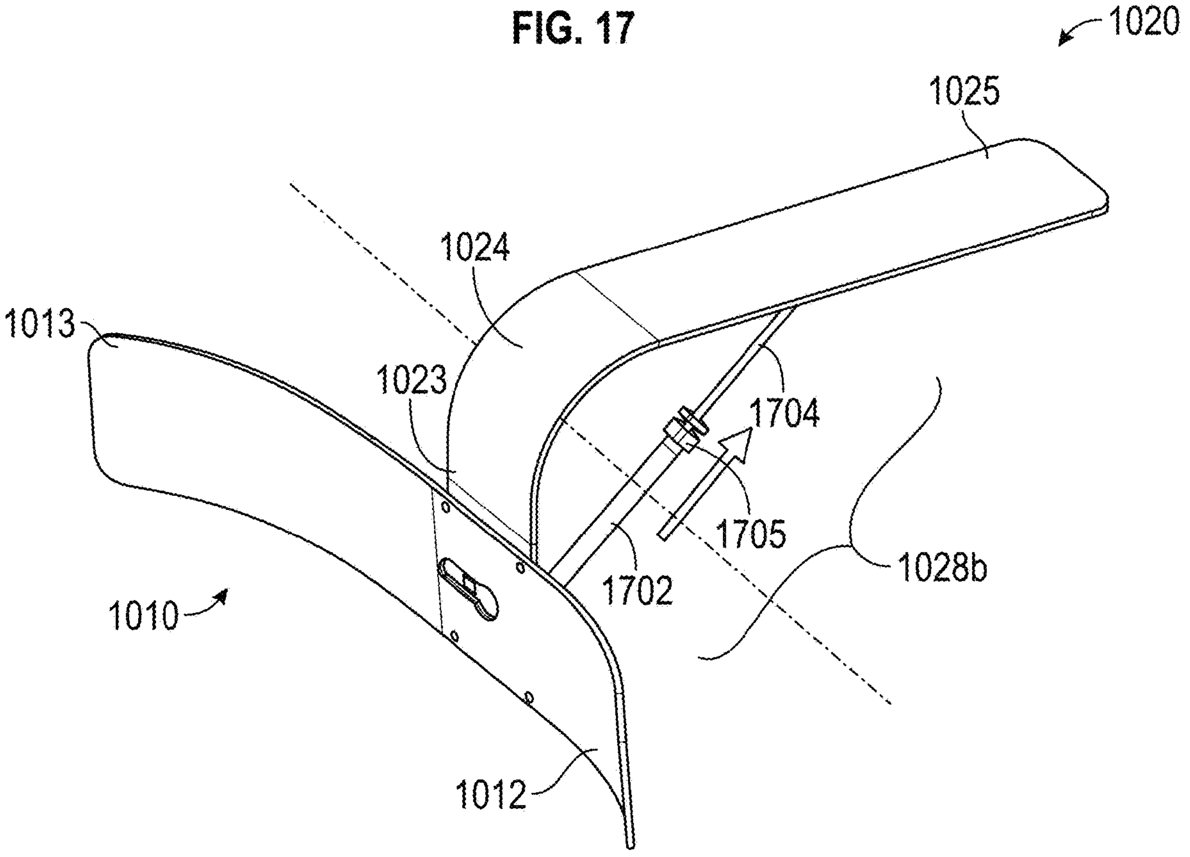
FIG. 18 illustrates another perspective view of the lockable rotating platform of FIG. 17, according to some example embodiments.

In yet other embodiments, for example, as shown in FIGS. 17 and 18, malleable semi-rigid supporting element 1020 comprises platform 1025, first curved portion 1024, first adjoining portion 1023 and rotation hub 1021 as previously described. However, in such embodiments, malleable semi-rigid supporting element 1020 may alternatively comprise a telescoping or extendable support strut 1028*b* in place of at least previously described forearm support strut 1028. Telescoping or extendable support strut 1028*b* is ultimately coupled between rotation hub 1021 and forearm support 1025 itself.

Telescoping or extendable support strut 1028*b* comprises a first portion 1702 configured to slide, extend, or otherwise telescope, with respect to a second portion 1704. First portion 1702 is configured to adjustably lock or adjustably fixate in any one of a plurality of continuous or incremental extended and/or telescoped configurations. For example, first portion 1702 is illustrated as comprising a tube or cylindrical feature having an inner diameter and second portion 1704 is illustrated as comprising a tube or cylindrical feature having an outer diameter smaller than the inner diameter of first portion 1702. However, such relative sizing may be reversed, such that first portion 1702 is sleeved within second portion 1704. Support strut 1028*b* further comprises a locking mechanism 1705, for example a collar that, when turned, clamps or holds first portion 1702 and second portion 1704 in the desired degree of extension.

In some embodiments, an end of first portion 1702 may be rotatably or pivotally coupled to rotation hub 1021 via a hinge 1706. An opposite end of second portion 1704 is, similarly, rotatably or pivotally coupled to forearm support platform 1030 via hinge 1708.

Accordingly, a difference in orientation between a plane in which second rotation hub 1021 extends and a plane in which telescoping or extending support strut 1028*b* extends is directly determined by the orientation of hinge 1706 and a difference in orientation between a plane in which telescoping and/or extending forearm support strut 1028*b* extends and a plane in which forearm platform 1025 extends is directly determined by the orientation of hinge 1708.

Accordingly, once rotation hub 1021 is fixed in a desired rotational orientation with respect to central portion 1011 and the desired orientation of forearm platform 1025 is achieved by bending first curved portion 1024, desired orientations of hinges 1706 and 1708 may be set such that telescoping forearm support strut 1028*b*, comprising first portion 1702 and second portion 1704 held in place by locking mechanism 1705, extends to or toward an underside of forearm platform 1025 to provide the user's arm a desired amount of abduction or adduction and a desired amount of internal or external rotation.

Figure 19:
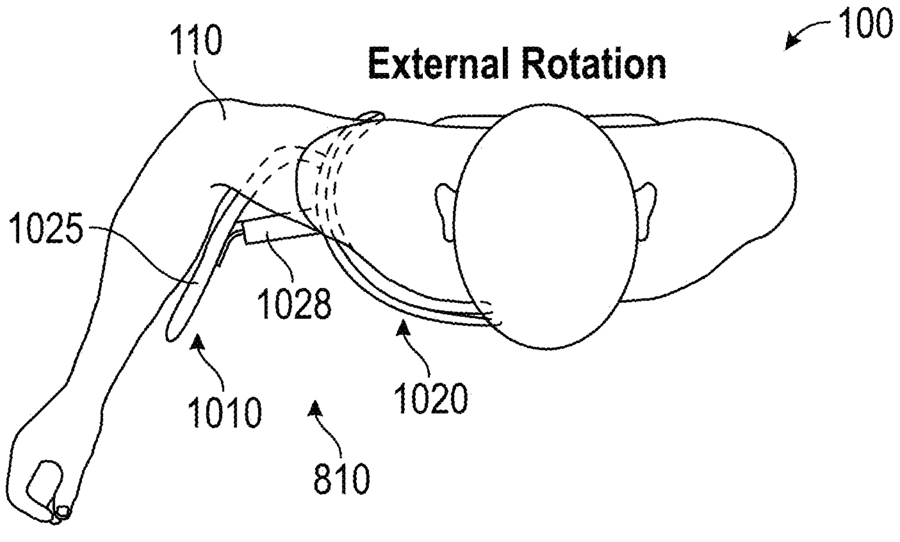
FIG. 19 illustrates a top-down view of a patient wearing any orthosis having a lockable rotating platform oriented to cause external rotation of the arm, according to some embodiments.
Figure 20:
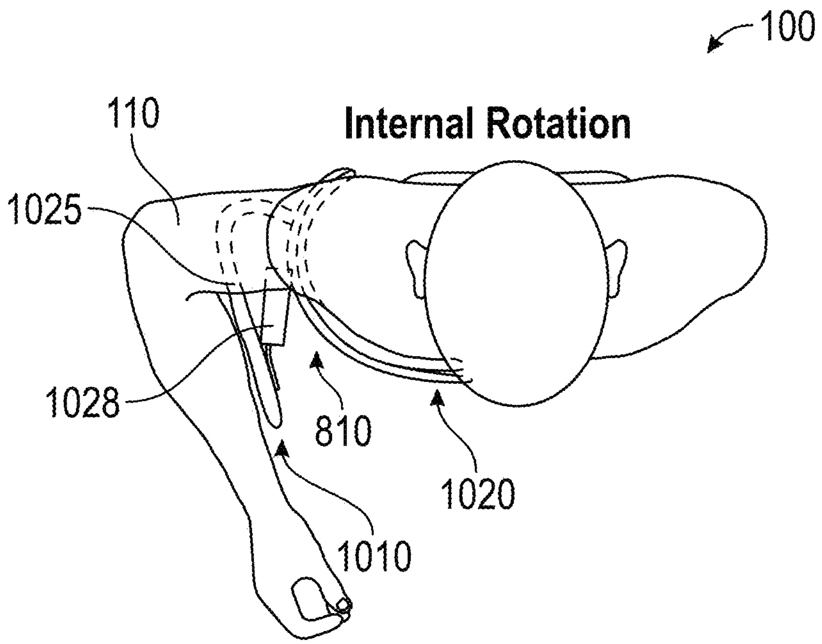
FIG. 20 illustrates a top-down view of a patient wearing any orthosis having a lockable rotating platform oriented to cause internal rotation of the arm, according to some embodiments.

FIG. 19 illustrates a top-down view of patient 100 wearing orthosis 800 with lockable rotating platform 810 oriented to cause a desired degree of external rotation of arm 110 of patient 100, according to some embodiments. And FIG. 20 illustrates a top-down view of patient 100 wearing orthosis 800 with lockable rotating platform 810 oriented to cause a desired degree of internal rotation of arm 110 of patient 100, according to some embodiments.

Figure 21:
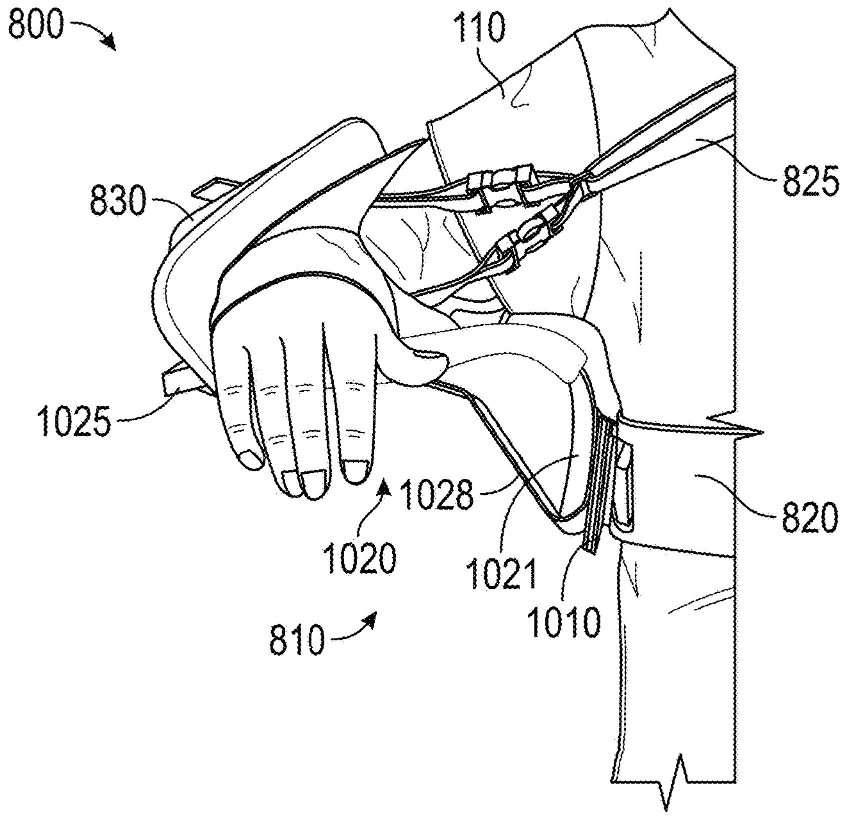
FIG. 21 illustrates the shoulder orthosis of FIG. 8 oriented on a patient to provide 90 degrees of arm abduction, according to some example embodiments.

However, notably, when orthosis 800 is in the position shown in FIG. 21, orthosis 800, may lose the ability to induce IR/ER angles with lockable rotated platform 810. FIG. 21 also illustrates the use of a shoulder belt 825 configured to be secured to forearm sling 830 at one end (e.g., see the y-straps diverging to couple on either side of forearm sling 830). Shoulder belt 825 is also configured to be secured around the neck and/or against a contralateral shoulder of the user.

Figure 22:
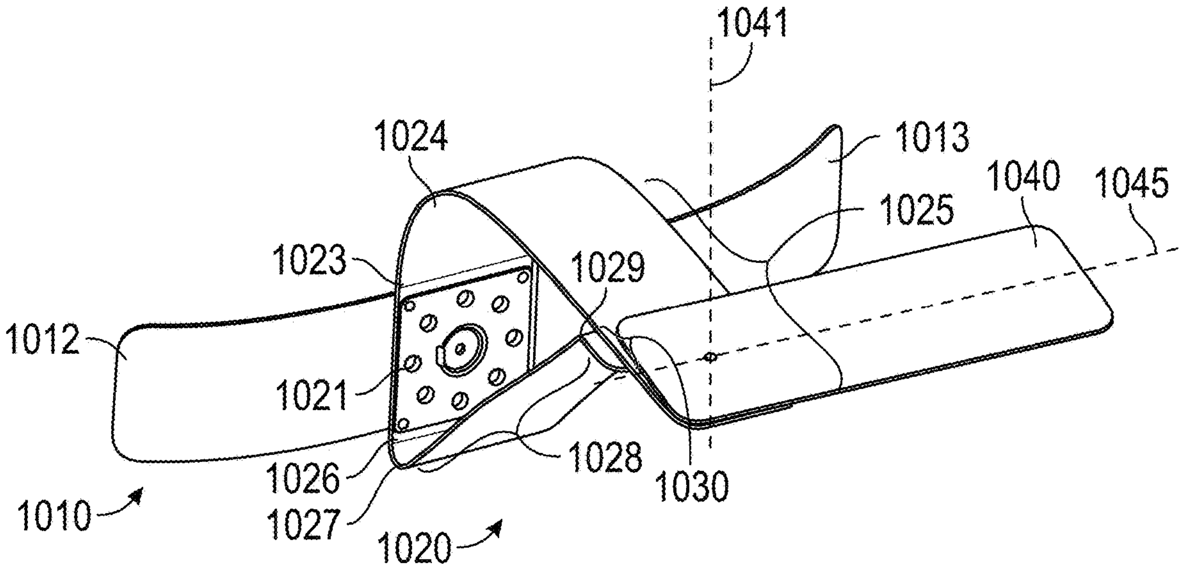
FIG. 22 illustrates a perspective view of the lockable rotating platform of FIG. 10 further including an additional malleable member, according to some example embodiments.

FIG. 22 illustrates embodiments wherein lockable rotating platform 810 further comprises an additional malleable member 1040 rotatably coupled, at a proximal portion thereof, to a distal portion of forearm platform 1025 such that additional malleable member 1040 may be rotated about an axis 1041 normal (i.e., perpendicular) to the surface of forearm platform 1025. Accordingly, as shown in FIG. 22, additional malleable member 1040 is configured to extend in a direction shown by axis 1045, which passes through and perpendicularly to the rotational axis 1041 of additional malleable member 1040. In the orientation shown in FIGS. 21 and 22, additional malleable member 1040 may provide a more stable secondary resting platform for the patient's forearm compared to forearm platform 1025 since, as shown in FIG. 21, forearm platform 1025 may support the upper portion of arm 110 and additional malleable member 1040 may support the lower portion (e.g., forearm) of arm 110. By contrast, when forearm platform 1025 is in other orientations, and for example free of additional malleable member 1025, forearm platform 1025 may be configured to support the lower portion (e.g., forearm) of arm 110. In some embodiments, additional malleable member 1040 is configured to maintain a planar form. In other embodiments, additional malleable member 1040 is also specifically configured to be reshaped in order to induce IR/ER angles at lower abduction angles, if needed or desired. Accordingly, additional malleable member 1040 may comprise a metal, such as but not limited to aluminum, thin steels and/or stainless steel and/or resin plastic.

In some embodiments, additional malleable member 1040 has a substantially constant width along its length of extension. In some embodiments, additional malleable member 1040 has a substantially constant thickness along its length of extension. In some embodiments, corners of additional malleable member 1040 may be rounded, e.g., similar to the rounded corners of torso conforming element 1010.

The rotating platform of this disclosure provides the ability to introduce up to 90 degrees of abduction of the shoulder joint compared to sagittal plane 320 of body 100 with the same platform that provides the IR and ER of arm 110 without the need to add or retrofit orthosis 800 with additional features, for example, as shown in FIGS. 4-7. In addition, by providing a rotating platform with positive locked positions, orthosis 800 (e.g., a brace) can be configured to be applied to both the right and left arm positions. This allows orthosis 800 to be truly universal and only requires the person applying orthosis 800 to rotate lockable rotating platform 810 to the desired position(s) and/or orientation(s), as described anywhere in this disclosure.

Moreover, one or more elements of the described orthoses may also be applied to other shoulder or elbow orthoses. And improvements brought about by the described orthoses can potentially provide improved methods for maintaining forearm stability while introducing relatively larger abduction angles and introducing similar methods of lockable IR/ER position with a similar pivoting platform.

Example Method(s) of Use and/or Manufacture

Figure 23:
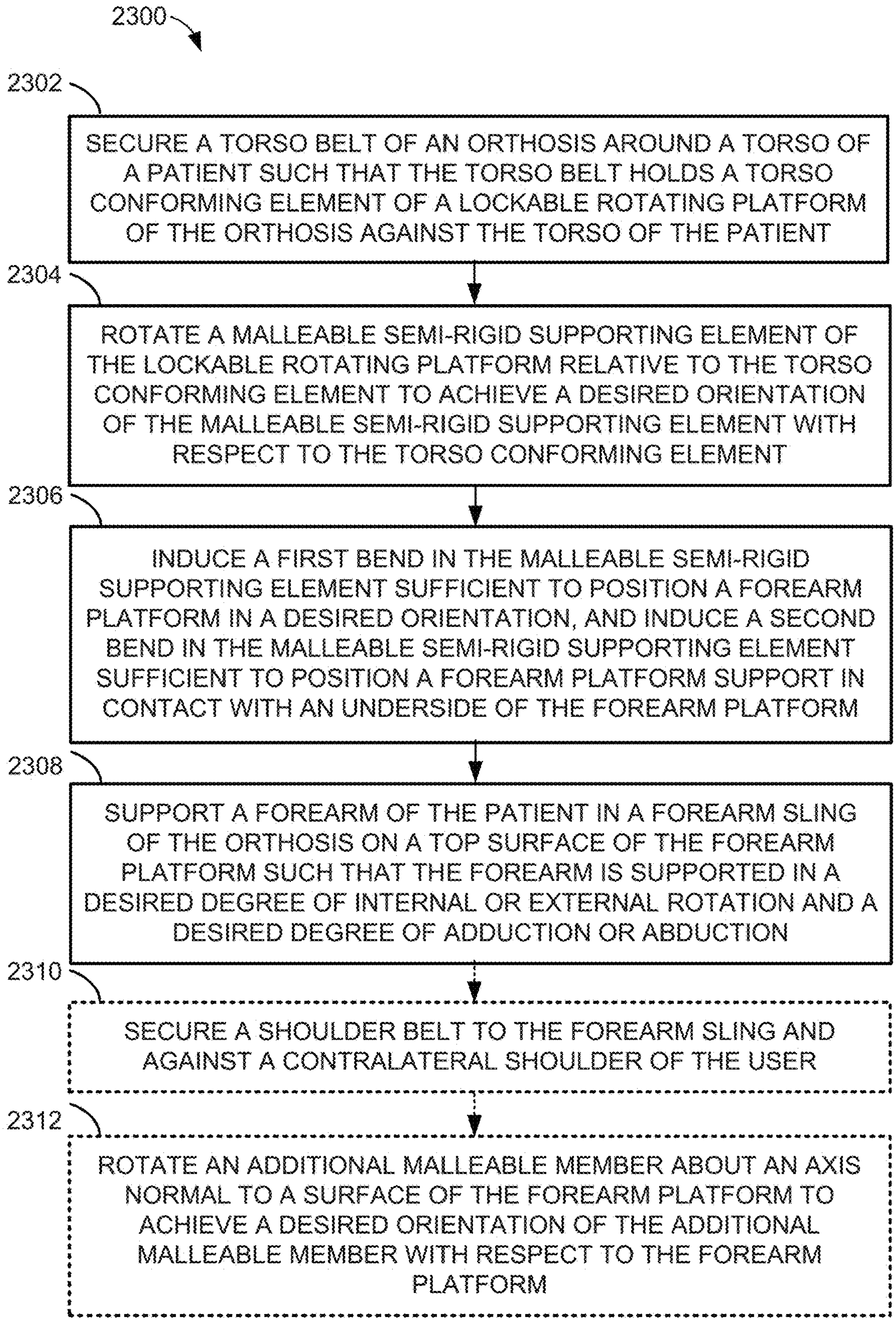
FIG. 23 illustrates a flowchart of a method of utilizing a shoulder orthosis as described anywhere in this disclosure, in accordance with some embodiments.

The disclosure now turns to FIG. 23, which illustrates a flowchart 2300 related to a method of utilizing an orthosis, as described anywhere in this disclosure. Although particular steps are described herein, the present application is not so limited and alternative methods may include a subset of these steps, in the same or different order, and may additionally include one or more addition steps not described herein, or to don, adjust and/or wear any portion of any orthosis described anywhere in this disclosure.

Step 2302 includes securing a torso belt 820 of the orthosis around a torso of a patient such that the torso belt holds a torso conforming element 1010 of a lockable rotating platform 810 of the orthosis against the torso of the patient. The torso conforming element comprises a central portion 1011, a first end 1012, and a second end 1013. The torso conforming element is curved along its length of extension between the first end and the second end to, thereby, conform to the torso of the patient.

Step 2304 includes rotating a malleable semi-rigid supporting element 1020 of the lockable rotating platform relative to the torso conforming element to achieve a desired orientation of the malleable semi-rigid supporting element with respect to the torso conforming element. At least a portion of the malleable semi-rigid supporting element is incorporated into the torso belt. The malleable semi-rigid supporting element includes a rotation hub 1021 rotatably coupled to the central portion of the torso conforming element, in some embodiments, about an axis that extends in a direction normal to a surface of the central portion, a first adjoining portion 1023 directly coupled to and extending away from the rotation hub in a same plane in which the rotation hub lies, the first adjoining portion continuously extending to become a first curved portion 1024, and the first curved portion continuously extending to become a forearm platform 1025, and a second adjoining portion 1026 directly coupled to and extending away from the rotation hub in the same plane but the opposite direction as the first adjoining portion, the second adjoining portion continuously extending to become a second curved portion 1027, the second curved portion continuously extending to become a forearm support strut 1028, the forearm support strut continuously extending to become a third curved portion 1029, and the third curved portion continuously extending to become a forearm platform support 1030. Accordingly, forearm platform 1025 is operatively connected to the rotation hub, and forearm support strut 1028 is operatively connected between the rotation hub and forearm support platform 1030.

Step 2306 includes inducing a first bend in malleable semi-rigid supporting element 1020 (e.g., to form the first curved portion 1024) sufficient to position the forearm platform 1025 in a desired orientation and inducing a second bend in malleable semi-rigid supporting element 1020 (e.g., to form the second curved portion 1027) sufficient to position the forearm platform support 1030 in contact with an underside of the forearm platform 1025.

In embodiments employing telescoping forearm support strut 1028*a* or 1028*b* rather than forearm support strut 1028, step 2306 may alternatively include inducing a bend in the first curved portion 1024 sufficient to position the forearm platform 1025 in a desired orientation and, either, inducing a bend in the second curved portion 1027 sufficient to position the forearm platform support 1030 in contact with an underside of the forearm platform 1025, or inducing an amount of rotation or pivot in the hinge 1706 coupling the end of the first portion 1702 of the telescoping support strut 1028*b* to malleable semi-rigid supporting element 1020 such that the telescoping support strut 1028*b* extends between the rotation hub 1021 and the forearm platform 1025.

Step 2308 includes supporting a forearm (110) of the patient in a forearm sling (830) of the orthosis on a top surface of the forearm platform (1025) such that the forearm (110) is supported in a desired degree of internal or external rotation and a desired degree of adduction or abduction.

In some embodiments, as illustrated in FIG. 23 by the dotted lines of the box and arrows leading thereto, a method related to flowchart 2300 may include step 2310, which includes securing a shoulder belt (825) to the forearm sling and against a contralateral shoulder of the user.

In some embodiments, as illustrated in FIG. 23 by the dotted lines of the box and arrows leading thereto, a method related to flowchart 2300 may include step 2312, which includes rotating an additional malleable member about an axis normal to a surface of the forearm platform to achieve a desired orientation of the additional malleable member with respect to the forearm platform.

Figure 24:
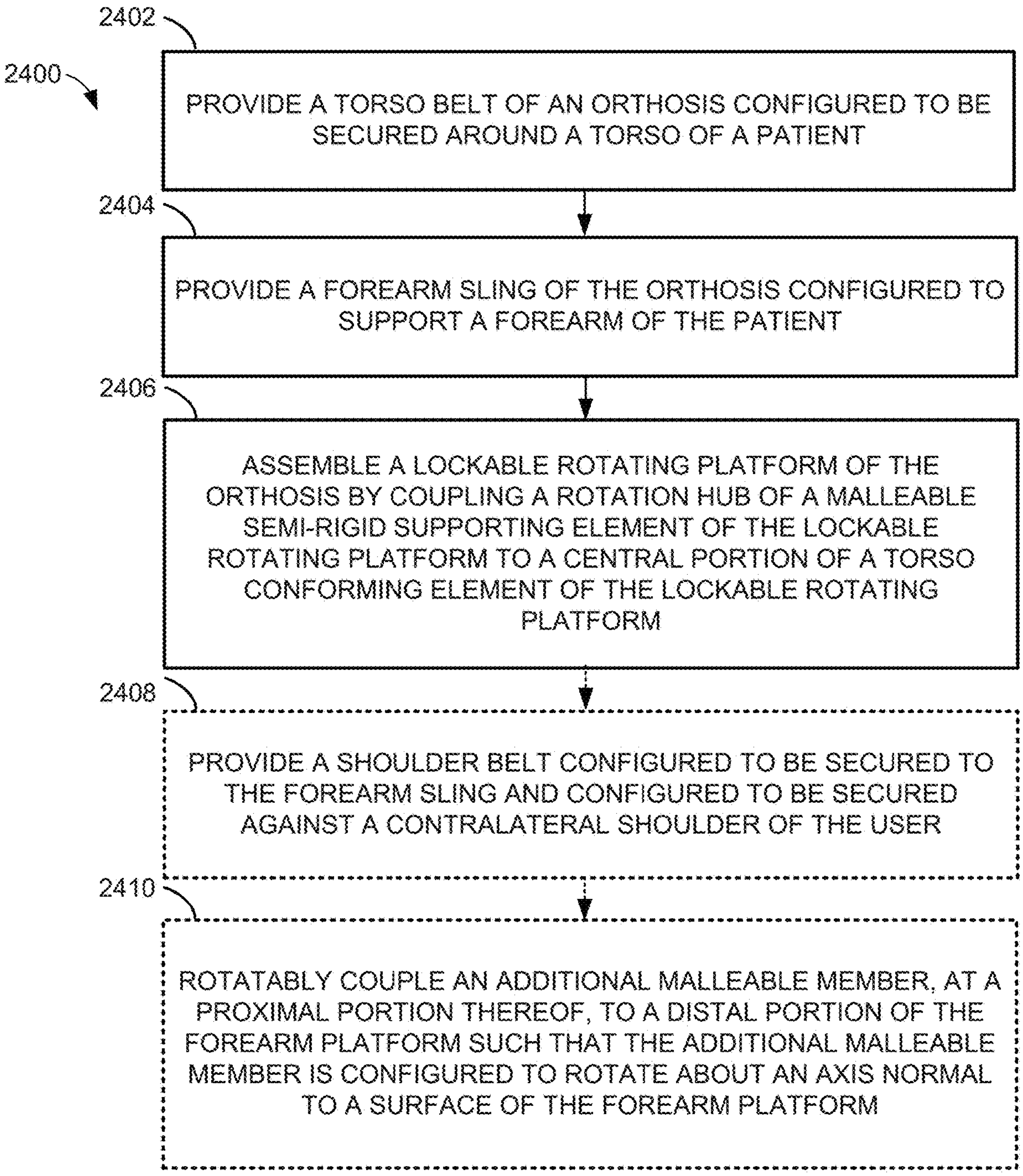
FIG. 24 illustrates a flowchart of a method of manufacturing a shoulder orthosis as described anywhere in this disclosure, in accordance with some embodiments.

The disclosure now turns to FIG. 24, which illustrates a flowchart 2400 related to a method of manufacturing an orthosis, as described anywhere in this disclosure. Although particular steps are described herein, the present application is not so limited and alternative methods may include a subset of these steps, in the same or different order, and may additionally include one or more addition steps not described herein, or to provide or otherwise manufacture any portion of any orthosis described anywhere in this disclosure.

Step 2402 includes providing a torso belt (820) of the orthosis configured to be secured around a torso of a patient.

Step 2404 includes providing a forearm sling (830) of the orthosis configured to support a forearm of the patient.

Step 2406 includes assembling a lockable rotating platform 810 of the orthosis by coupling a rotation hub 1021 of a malleable semi-rigid supporting element 1020 of the lockable rotating platform to a central portion 1011 of a torso conforming element 1010 of the lockable rotating platform, in some embodiments, about an axis that extends in a direction normal to a surface of the central portion. The torso conforming element 1010 is configured to be held e.g., directly against a substantially uninterrupted extent of the torso of the patient by the torso belt. The torso conforming element further comprises, a central portion 1011, a first end 1012, and a second end 1013, wherein the torso conforming element is curved along its length of extension between the first end and the second end to, thereby, conform to the substantially uninterrupted extent of the torso of the patient. The malleable semi-rigid supporting element further comprises a first adjoining portion 1023 directly coupled to and extending away from the rotation hub in a same plane in which the rotation hub lies and a second adjoining portion 1026 directly coupled to and extending away from the rotation hub in the same plane but the opposite direction as the first adjoining portion. The first adjoining portion continuously extends to become a first curved portion 1024 and the first curved portion continuously extends to become a forearm platform 1025. The second adjoining portion continuously extends to become a second curved portion 1027, the second curved portion continuously extends to become a forearm support strut 1028, the forearm support strut continuously extends to become a third curved portion 1029, and the third curved portion continuously extends to become a forearm support platform 1030. Accordingly, forearm platform 1025 is operatively connected to the rotation hub, and forearm support strut 1028 is operatively connected between the rotation hub and forearm support platform 1030.

In some embodiments, as illustrated in FIG. 24 by the dotted lines of the box and arrows leading thereto, a method related to flowchart 2400 may include a step 2408, which includes providing a shoulder belt 825 configured to be secured to the forearm sling 830 and configured to be secured against a contralateral shoulder of the user.

In some embodiments, as illustrated in FIG. 24 by the dotted lines of the box and arrows leading thereto, a method related to flowchart 2400 may include a step 2410, which includes rotatably coupling an additional malleable member 1040, at a proximal portion thereof, to a distal portion of the forearm platform such that the additional malleable member is configured to rotate about an axis normal to a surface of the forearm platform.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

What is claimed is:

1. An orthosis, comprising:

a torso belt configured to be secured around a torso of a patient;

a forearm sling configured to support a forearm of the patient; and a lockable rotating assembly, comprising:

a torso conforming element configured to be held against the torso of the patient by the torso belt, the torso conforming element comprising:

a central portion, a first end, and a second end, wherein the torso conforming element is curved along a length of extension between the first end and the second end to, thereby, conform to the torso of the patient;

a malleable semi-rigid supporting element, the malleable semi-rigid supporting element comprising:

a rotation hub rotatably coupled to the central portion of the torso conforming element, a forearm platform operatively connected to the rotation hub, and a forearm support strut operatively connected between the rotation hub and a forearm support platform, the forearm support strut comprising a first hook or loop material; and a forearm support strut extension comprising a second hook or loop material complementary to the first hook or loop material, the forearm support strut extension configured to adjustably fixate in any one of a plurality of continuous extended configurations with respect to the forearm support strut via the first and second hook or loop materials, the forearm support strut extension extending to become a curved portion, which extends to become a forearm support strut extension platform.

2. The orthosis of claim 1, wherein the malleable semi-rigid supporting element comprises a first adjoining portion coupled to and extending away from the rotation hub to become a first curved portion, the first curved portion extending to become the forearm platform.

3. The orthosis of claim 2, wherein the malleable semi-rigid supporting element comprises a second adjoining portion coupled to and extending away from the rotation hub in an opposite direction of the first adjoining portion, the second adjoining portion extending to become a second curved portion, the second curved portion extending to become the forearm support strut, the forearm support strut extending to become a third curved portion, and the third curved portion extending to become the forearm support platform.

4. The orthosis of claim 3, wherein at least one of the first adjoining portion and the second adjoining portion extends away from the rotation hub in a same plane in which the rotation hub lies.

5. The orthosis of claim 3, wherein the forearm support strut is planar such that a difference in orientation between a plane in which the second adjoining portion extends and a plane in which the forearm support strut extends is directly determined by an amount of curvature induced in the intervening second curved portion.

6. The orthosis of claim 3, wherein the forearm support platform is planar such that a difference in orientation between a plane in which the forearm support strut extends and a plane in which the forearm support platform extends is directly determined by an amount of curvature induced in the intervening third curved portion.

7. The orthosis of claim 3, wherein the forearm support strut extends from the second curved portion to an underside of the forearm platform, and the forearm support platform is disposed against and in parallel with the underside of the forearm platform.

8. The orthosis of claim 3, wherein the second curved portion and the third curved portion are each curved in a single dimension such that the second curved portion and the third curved portion do not possess compound curvature and such that the second curved portion and the third curved portion are each substantially flat along a direction perpendicular to the single dimension of curvature.

9. The orthosis of claim 2, wherein the forearm platform is planar such that a difference in orientation between a plane in which the first adjoining portion extends and a plane in which the forearm platform extends is directly determined by an amount of curvature induced in the intervening first curved portion.

10. The orthosis of claim 2, wherein the first curved portion is configured to be bent to a desired degree sufficient to dispose the forearm platform in a desired orientation.

11. The orthosis of claim 2, wherein the first curved portion is curved in a single dimension such that the first curved portion does not possess compound curvature and such that the first curved portion is substantially flat along a direction perpendicular to the single dimension of curvature.

12. The orthosis of claim 1, wherein the lockable rotating assembly further comprises an additional malleable member rotatably coupled, at a proximal portion thereof, to a distal portion of the forearm platform such that the additional malleable member is configured to rotate about an axis normal to a surface of the forearm platform.

13. The orthosis of claim 12, wherein the additional malleable member is sufficiently malleable, and configured to be bent to a desired shape.

14. The orthosis of claim 1, wherein the orthosis is a shoulder brace.

15. The orthosis of claim 1, wherein the rotation hub is rotatably coupled to the central portion of the torso conforming element about an axis that extends normal to a surface of the central portion.

16. The orthosis of claim 1, wherein the forearm support strut and the forearm support platform are a monolithic, unitary component.

17. The orthosis of claim 1, wherein the torso conforming element and the malleable semi-rigid supporting element each comprises a malleable metal.

18. The orthosis of claim 1, further comprising a shoulder belt configured to be secured to the forearm sling and configured to be secured against a contralateral shoulder of the user.

19. The orthosis of claim 1, wherein the torso conforming element is sufficiently malleable to be bent into a curvature required to conform to the torso of the patient.

20. The orthosis of claim 1, wherein the torso conforming element has a substantially constant width along the length of extension between the first end and the second end.

21. The orthosis of claim 1, wherein the torso conforming element has a substantially constant thickness along the length of extension between the first end and the second end.

22. The orthosis of claim 1, wherein corners of at least one of the first end and the second end of the torso conforming element have a radius of curvature sufficiently large to prevent the corners from poking into the torso of the patient while wearing the orthosis.

23. The orthosis of claim 1, wherein the rotation hub of the malleable semi-rigid supporting element is substantially planar and disposed parallel to the central portion of the torso conforming element.

24. The orthosis of claim 1, wherein the central portion of the torso conforming element comprises a protruding pin and wherein the rotation hub comprises a plurality of detents, each configured to receive the protruding pin when the rotation hub is disposed in a respective lockable rotational orientation with respect to the torso conforming element to, thereby, lock the rotation hub of the malleable semi-rigid supporting element in a desired one of the lockable rotational orientations with respect to the central portion of the torso conforming element.

25. The orthosis of claim 1, wherein the malleable semi-rigid supporting element comprises a single, monolithic element having a substantially constant width along a length of extension between a distal end of the forearm platform and a distal end of the forearm support platform.

26. The orthosis of claim 1, wherein the malleable semi-rigid supporting element has a substantially constant thickness along a length of extension between a distal end of the forearm platform and a distal end of the forearm support platform.

27. The orthosis of claim 1, wherein corners of a distal end of the forearm platform have a radius of curvature sufficiently large to prevent the corners from poking into the forearm of the patient while wearing the orthosis.

28. A method of utilizing an orthosis, the method comprising:
- securing a torso belt of the orthosis around a torso of a patient such that the torso belt holds a torso conforming element of a lockable rotating assembly of the orthosis against the torso of the patient, wherein the torso conforming element comprises:
  - a central portion,
  - a first end, and
  - a second end, the torso conforming element being curved along a length of extension between the first end and the second end to, thereby, conform to the torso of the patient;
- rotating a malleable semi-rigid supporting element of the lockable rotating assembly relative to the torso conforming element to achieve a desired orientation of the malleable semi-rigid supporting element with respect to the torso conforming element, the malleable semi-rigid supporting element comprising:
  - a rotation hub rotatably coupled to the central portion of the torso conforming element,
  - a forearm platform operatively connected to the rotation hub, and
    - a forearm support strut operatively connected between the rotation hub and a forearm support platform, the forearm support strut comprising a first hook or loop material;
- inducing a first bend in the malleable semi-rigid supporting element sufficient to position the forearm platform in a desired orientation and inducing a second bend in the malleable semi-rigid supporting element sufficient to position the forearm support platform between the rotation hub and the forearm platform;
- adjustably fixate a forearm support strut extension comprising a second hook or loop material, complementary to the first hook or loop material, in any one of a plurality of continuous extended configurations with respect to the forearm support strut via the first and second hook or loop materials, the forearm support strut extension extending to become a curved portion, which extends to become a forearm support strut extension platform that is in contact with an underside of the forearm platform; and
- supporting a forearm of the patient in a forearm sling of the orthosis on a top surface of the forearm platform such that the forearm is supported in a desired degree of internal or external rotation and a desired degree of adduction or abduction.

29. A method of manufacturing an orthosis, comprising:
- providing a torso belt of the orthosis configured to be secured around a torso of a patient;
- providing a forearm sling of the orthosis configured to support a forearm of the patient;
- assembling a lockable rotating assembly of the orthosis by coupling a rotation hub of a malleable semi-rigid supporting element of the lockable rotating assembly to a central portion of a torso conforming element of the lockable rotating assembly, wherein:
  - the torso conforming element is configured to be held against the torso of the patient by the torso belt,
  - the torso conforming element further comprises:
    - a first end, and
    - a second end, wherein the torso conforming element is curved along a length of extension between the first end and the second end to, thereby, conform to the torso of the patient; and
  - the malleable semi-rigid supporting element further comprises:
    - a forearm platform operatively connected to the rotation hub, and
    - a forearm support strut operatively connected between the rotation hub and a forearm support platform, the forearm support strut comprising a first hook or loop material; and
- providing a forearm support strut extension comprising a second hook or loop material, complementary to the first hook or loop material, the forearm support strut extension configured to adjustably fixate in any one of a plurality of continuous extended configurations with respect to the forearm support strut via the first and second hook or loop materials, the forearm support strut extension extending to become a curved portion, which extends to become a forearm support strut extension platform.

* * * * *